US012515021B2

(12) United States Patent
Castro et al.

(10) Patent No.: US 12,515,021 B2
(45) Date of Patent: Jan. 6, 2026

(54) WIRE INTRODUCTION DEVICE

(71) Applicant: SonoStik LLC, North Potomac, MD (US)

(72) Inventors: Nathan J. Castro, Washington, DC (US); Benjamin B. Holmes, Washington, DC (US); Neal K. Sikka, Vienna, VA (US); Alfred P. Stancampiano, Newton, MA (US); Richard L Fogel, North Potomac, MD (US); Alan D. Fortunate, Brighton, MA (US); Hawaa Almansouri, Abu Dhabi (AE); Adam Corman, McLean, VA (US)

(73) Assignee: Sonostik LLC, Canfield, OH (US)

( * ) Notice: Subject to any disclaimer, the term of this patent is extended or adjusted under 35 U.S.C. 154(b) by 0 days.

(21) Appl. No.: 17/985,643

(22) Filed: Nov. 11, 2022

(65) Prior Publication Data

US 2023/0071736 A1 Mar. 9, 2023

Related U.S. Application Data

(63) Continuation of application No. 16/598,215, filed on Oct. 10, 2019, now Pat. No. 11,497,897, which is a (Continued)

(51) Int. Cl.
*A61M 25/09* (2006.01)
*A61M 25/01* (2006.01)
*A61M 25/06* (2006.01)

(52) U.S. Cl.
CPC .. *A61M 25/09041* (2013.01); *A61M 25/0113* (2013.01); *A61M 25/0606* (2013.01); (Continued)

(58) Field of Classification Search
CPC ............ A61B 17/3415; A61B 17/3417; A61B 2017/3419; A61B 17/3421; (Continued)

(56) References Cited

U.S. PATENT DOCUMENTS 4,417,886 A 11/1983 Frankhouser et al.
4,586,923 A 5/1986 Gould et al.
(Continued)

FOREIGN PATENT DOCUMENTS

CN 105286996 2/2016
WO WO 1994/016762 8/1994
(Continued)

OTHER PUBLICATIONS

Arrow International Inc.—Products—Central Venous Access, Central Venous Access Catheters, website: www.arrowintl.com/products/cvc, 2 pages, printed Feb. 25, 2014.
(Continued)

*Primary Examiner* — Jeffrey G. Hoekstra
(74) *Attorney, Agent, or Firm* — Fish & Richardson P.C.

(57) ABSTRACT

A deep vein intravenous introducer has a wheel located toward the front end of the device that can be rotated by the index finger of the user. After placement of the needle in the lumen of the vessel, the user rotates the wheel, which turns a drive wheel. The drive wheel has an outer surface that advances the guide wire through the center of the needle and into the patient. Once the guide wire is advanced into the vessel lumen the catheter can be advanced over the guide wire with a hub or finger tab on the catheter close to the index finger. The operation can be performed by one hand without moving the hand from its initial position.

22 Claims, 11 Drawing Sheets

Related U.S. Application Data continuation of application No. 16/162,194, filed on Oct. 16, 2018, now Pat. No. 10,441,756, which is a continuation of application No. 14/885,603, filed on Oct. 16, 2015, now Pat. No. 10,143,826.

(60) Provisional application No. 62/073,103, filed on Oct. 31, 2014.

(52) U.S. Cl.
CPC ............... *A61M 2025/0681* (2013.01); *A61M 2025/09116* (2013.01)

(58) Field of Classification Search
CPC .......... A61M 25/0113; A61M 25/0606; A61M 25/065; A61M 2025/0687; A61M 2025/0681; A61M 25/0662; A61M 25/09041
See application file for complete search history.

(56) References Cited

U.S. PATENT DOCUMENTS

| | | | |
|---|---|---|---|
| 4,616,648 | A | 10/1986 | Simpson |
| 4,772,264 | A | 9/1988 | Cragg |
| 5,199,950 | A | 4/1993 | Schmitt et al. |
| 5,199,960 | A | 4/1993 | Farng et al. |
| 5,318,541 | A | 6/1994 | Viera et al. |
| 5,346,498 | A | 9/1994 | Greelis et al. |
| 5,389,087 | A | 2/1995 | Miraki |
| 5,462,527 | A | 10/1995 | Stevens-Wright |
| 6,110,121 | A | 8/2000 | Lenker |
| 6,533,772 | B1 | 3/2003 | Sherts et al. |
| 6,592,526 | B1 | 7/2003 | Lenker |
| 6,833,772 | B1 | 12/2004 | Brown et al. |
| 7,175,635 | B2 | 2/2007 | Loser |
| 7,506,650 | B2 | 3/2009 | Lowe et al. |
| 7,524,289 | B2 | 4/2009 | Lenker |
| D598,543 | S | 8/2009 | Vogel et al. |
| 7,604,611 | B2 | 10/2009 | Falwell et al. |
| 7,674,282 | B2 | 3/2010 | Wu et al. |
| 7,758,625 | B2 | 7/2010 | Wu et al. |
| 7,867,169 | B2 | 1/2011 | Webler et al. |
| 7,935,141 | B2 | 5/2011 | Randall et al. |
| 7,967,829 | B2 | 6/2011 | Gunderson et al. |
| 7,976,574 | B2 * | 7/2011 | Papp ......................... A61F 2/95 623/1.11 |
| 7,993,384 | B2 | 8/2011 | Gunderson et al. |
| 8,057,395 | B2 | 11/2011 | Lenker |
| 8,303,509 | B2 | 11/2012 | Webler et al. |
| 8,382,674 | B2 | 2/2013 | Webler |
| 8,430,863 | B2 | 4/2013 | Webler |
| 8,500,789 | B2 | 8/2013 | Wuebbeling et al. |
| 8,535,327 | B2 | 9/2013 | Schaller et al. |
| D692,559 | S | 10/2013 | Scheibel et al. |
| 8,728,035 | B2 | 5/2014 | Warring et al. |
| 8,784,468 | B2 | 7/2014 | Gerdts et al. |
| 8,888,834 | B2 | 11/2014 | Hansen et al. |
| D719,651 | S | 12/2014 | Blanchard et al. |
| 8,932,258 | B2 | 1/2015 | Blanchard et al. |
| 8,998,852 | B2 | 4/2015 | Blanchard et al. |
| D733,289 | S | 6/2015 | Blanchard |
| 9,050,438 | B2 | 6/2015 | Rollins et al. |
| D735,321 | S | 7/2015 | Blanchard |
| 9,119,942 | B1 | 9/2015 | Rollins et al. |
| 9,162,037 | B2 | 10/2015 | Belson et al. |
| D751,195 | S | 3/2016 | Lai et al. |
| 9,314,306 | B2 | 4/2016 | Yu |
| 9,326,874 | B2 | 5/2016 | Parker et al. |
| 10,092,731 | B2 | 10/2018 | Almansouri et al. |
| 10,143,826 | B2 | 12/2018 | Castro et al. |
| 10,441,756 | B2 | 10/2019 | Castro et al. |
| 11,191,928 | B2 | 12/2021 | Almansouri et al. |
| 12,251,262 | B2 * | 3/2025 | Singh .................. A61B 8/0841 |
| 2003/0036712 | A1 | 2/2003 | Heh et al. |
| 2004/0082880 | A1 | 4/2004 | Heh et al. |
| 2005/0024587 | A1 | 2/2005 | Somani |
| 2005/0080476 | A1 | 4/2005 | Gunderson et al. |
| 2005/0245847 | A1 | 11/2005 | Schaeffer |
| 2007/0055342 | A1 | 3/2007 | Wu et al. |
| 2007/0260225 | A1 | 11/2007 | Sakakine et al. |
| 2008/0262431 | A1 | 10/2008 | Anderson et al. |
| 2008/0319387 | A1 | 12/2008 | Amisar et al. |
| 2009/0099641 | A1 | 4/2009 | Wu et al. |
| 2009/0187168 | A1 | 7/2009 | Maeda |
| 2009/0210046 | A1 | 8/2009 | Shumer et al. |
| 2009/0216125 | A1 | 8/2009 | Lenker |
| 2010/0004606 | A1 | 1/2010 | Hansen et al. |
| 2010/0094310 | A1 | 4/2010 | Warring et al. |
| 2010/0168834 | A1 | 7/2010 | Ryan et al. |
| 2010/0174290 | A1 | 7/2010 | Wuebbling et al. |
| 2010/0241177 | A1 | 9/2010 | Schaller et al. |
| 2011/0172542 | A1 | 7/2011 | Racz |
| 2011/0288533 | A1 | 11/2011 | Koch et al. |
| 2011/0307069 | A1 | 12/2011 | Frassica et al. |
| 2012/0041537 | A1 | 2/2012 | Parker et al. |
| 2013/0317592 | A1 | 11/2013 | Wubbeling et al. |
| 2014/0094774 | A1 | 4/2014 | Blanchard |
| 2015/0038943 | A1 | 2/2015 | Warring et al. |
| 2015/0051584 | A1 | 2/2015 | Korkuch et al. |
| 2015/0051688 | A1 | 2/2015 | Cummins |
| 2015/0119806 | A1 | 4/2015 | Blanchard et al. |
| 2015/0202414 | A1 | 7/2015 | Hwang |
| 2015/0231364 | A1 | 8/2015 | Blanchard et al. |
| 2015/0306356 | A1 | 10/2015 | Gill |
| 2015/0320579 | A1 | 11/2015 | Wubbeling et al. |
| 2016/0015943 | A1 | 1/2016 | Belson et al. |
| 2016/0015945 | A1 | 1/2016 | Warring et al. |
| 2019/0083755 | A1 | 3/2019 | Castro et al. |

FOREIGN PATENT DOCUMENTS

| | | | | |
|---|---|---|---|---|
| WO | WO-0018463 A1 * | 4/2000 | ........ A61M 25/0113 |
| WO | WO-2006085331 A2 * | 8/2006 | ........ A61M 25/0606 |
| WO | WO 2013/100233 | 7/2013 | |
| WO | WO 2014/134275 | 9/2014 | |

OTHER PUBLICATIONS

Beehive Medical Solutions—Ultrasound Supplies—Ultrasound probe covers—Latex Probe Co., website: www.beehive-solitions.co.uk/catalog/product_info.php?pName=ultrasound-probe-c, 2 pages printed Feb. 25, 2014.

Central Venous Access Catheters, Arrow International Inc.—Products—Central Venous Access, website: www.arrowintl.com/products/cvc, 2 pages, printed Feb. 25, 2014.

Central Venous Cathertization Kits by Teleflex, website: www.medline.com/jump/product/x/Z05-Pf42500, pp. 1-2, printed Feb. 19, 2014.

CIVCO Medical Solutions, Multi-Modality Imaging, Ultrasound Imaging Accessories Catalog, vol. 9, 56 pages.

CIVCO Medical Solutions, Multi-Modality Imaging, Infection Control, 6 pages, © 2012.

CIVCO Reference Guide, Latex Transducer Covers, pp. 1-20, © 2012.

Ecolab, Microtek, Ultracover, 4 pages, © 2009.

European Search Report Issued in European Application No. 14757653.2 dated Dec. 1, 2016, 9 pages.

European Supplementary Partial Search Report in European Application No. EP15856147, dated Aug. 20, 2018, 21 pages.

International Search Report for PCT/US2015/056874 dated Feb. 4, 2016, 8 pages.

International Search Report PCT/US 15/18047 dated Jun. 10, 2015.

International Search Report PCT/US2014/018931 dated Aug. 20, 2014.

Jelco I.V. Catheters, Peripheral I.V. Catheters, website: www.smiths-medical.com/catalog/peripheral-catherters/conventional-catheters/jelco, pp. 1-9, printed Feb. 25, 2014.

List of IV Catheters, website: www.medline.com/product/Insyte153-Autoguard153-Shielded -IV-Catheters-by-Beet, pp. 1-7, printed Feb. 25, 2014.

(56) References Cited

OTHER PUBLICATIONS

Microtek Medical—A Division of Ecolab, TOE Cover, Trans Oesophageal Echocardiography Probecover, 2 pages, © 2009.
PowerHohn, Central Venous Catheter, Central Venous Catheters, Bard Access Systems, website:www.bardaccess.com/picc-powerhohn,php, 3 pages printed Feb. 25, 2014.
Sterile T shaped Surgi Transducer Covers, "sterile T-Shaped Surgia," website: www.civci.com/mmi/ultrasound/covers/surgical/steile-tshaped-surgi-transducer-co, 2 pages, printed Feb. 25, 2014.
Teleflex Medical, Cardiac Care, Arrow Transradial Artery Access Kits, 2 pages, © 2010.
Teleflex, Introducing the Arrow Ergopack System, Central Venous Catheter, 1 page, © 2010.
Ultrasound Probe Equipment Drapes by Microtek Medical, Equipment Drapes—Ultrasound Probe Covers, website: www.microtekmed.com/uk/prod_equiltraprobe.htm, 1 page, printed Feb. 25, 2014.

* cited by examiner

Figure 19
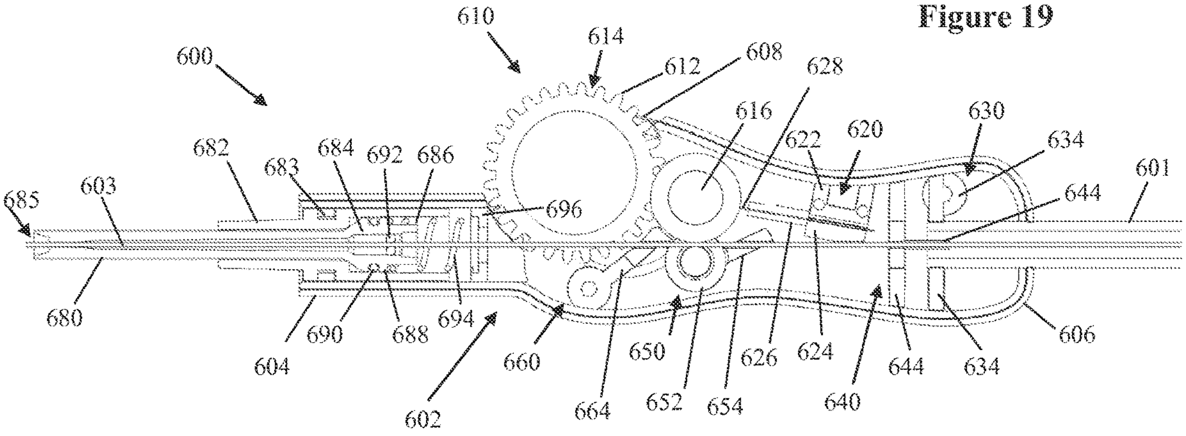
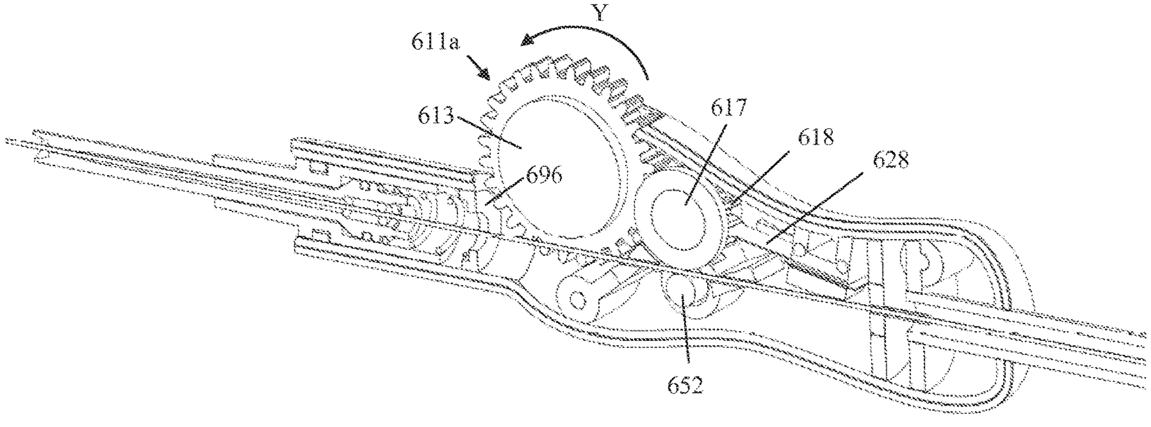
Figure 20

WIRE INTRODUCTION DEVICE

RELATED APPLICATIONS

This application is a continuation of U.S. application Ser. No. 16/598,215, filed on Oct. 10, 2019 which is a continuation of U.S. application Ser. No. 16/162,194, filed on Oct. 16, 2018, which claims priority to U.S. application Ser. No. 14/885,603, filed Oct. 16, 2015, which claims priority to U.S. Provisional Application No. 62/073,103, filed Oct. 31, 2014 and is related to International Application No. PCT/US2014/018931, filed Feb. 27, 2014, which claims priority to U.S. Provisional Application No. 61/770,052, filed Feb. 27, 2013. The entire contents of those applications are incorporated herein by reference.

BACKGROUND OF THE INVENTION

Field of the Invention

This invention relates to a system, device and method for the introduction of catheters and more particularly to the introduction of catheters into small diameter blood vessels, deep vessels, central veins, arteries, and those visualized by ultrasound.

Background of the Related Art

Catheter introduction sets are generally known. For instance, U.S. Pat. No. 4,417,886 discloses a catheter introduction set having a needle, catheter, wire guide and wire guide feed device in which when the needle is positioned into a lumen of a blood vessel, a wire guide is first inserted into the vessel and the catheter is fed over the wire guide from the use of a radially extended handle into the lumen. This arrangement is similarly disclosed in U.S. Pat. No. 4,772,264 with the addition of a retaining finger for stabilization of the catheter on the skin.

However, these catheter introduction sets require the user to use two hands to operate the device. One hand is needed to insert the needle and catheter, and a second hand to feed the guide wire. This means that one hand has to be taken off the ultrasound probe to feed the guide wire. Consequently, a single user cannot visualize the guide wire directly while threading the vessel, which increases the possibility of misplacement of the guide wire.

Catheters, both central and peripheral, are not designed to be visualized under ultrasound and correct placement is essential for proper medication administration. A catheter can be placed into a vessel with an introducer needle with or without a guide wire. The guide wire and the introducer needle can be visualized under ultrasound, but the catheter itself cannot be visualized. Because the catheter cannot be visualized, sometimes catheters are placed incorrectly. Examples of incorrect catheter placement include: in an artery instead of a vein, in a vein instead of an artery, and in neither a vein nor an artery. Arteries flow next to veins and can be easily catheterized accidentally when aiming for a vein. Accidental placement of a catheter in an artery instead of a vein can lead to destruction of tissues receiving blood from that artery due to application of medications that damage arteries and are intended only for use in veins.

While placing an ultrasound guided IV catheter there are two directional variables the health care professional has to deal with: longitudinal and vertical. Without the use of a directional marker the physician can become disoriented to the longitudinal direction. There is a simple method to alleviate this complication by using a directional marker to orient the longitudinal direction of the catheter to the vessel, eliminating this variable and simplifying the ultrasound guidance technique. Two temporary points can be marked on the surface of the skin one at the point of planned initial entry of the catheter over the vessel and another small distance distal to this point. The ultrasound can be used to follow the vessel allowing the clinician to mark these two points above the vessel on the skin. However, currently available catheter introduction sets do not incorporate a means to make directional markings on the skin.

Stable position of the body part to be catheterized is essential for both placement of the catheter and comfort of the patient. Catheter introduction kits are available manufactured by Arrow International for the radial artery. These kits include a case that both holds the kit contents and provides means to stabilize the wrist for the catheter insertion in the artery of the wrist. Currently there are no kits available for catheter introduction in the anti-cubital veins of the upper arm. Because no such kits are available, practitioners do not have readily available means to stabilize the arm for catheterization. Likewise, additional body parts that are catheterized besides the arm, also do not have kits available that provide body part stabilizing means.

Ultrasound guided vascular access and other procedures must be done in an expedited fashion for medical purposes. Often the speed of vascular access can be a matter of life or death. This procedure is invasive, meaning that there is the chance of bacteria being introduced from the skin into the vessel, which is why the procedure must be performed under sterile conditions. Ultrasound probes used repeatedly have a propensity to be contaminated. For this reason sterile probe covers are used to prevent infection. Current probe covers for probes used in ultrasound guided vascular access are large, bulky and time consuming to put on. These probe covers are very long in order to cover not only the transducer end of the probe, but also much of the cord.

A fast time to catheter placement is essential in the health care setting for the administration of medications especially in sick patients, and patients in pain, who have rapidly spreading medical conditions. When placing an ultrasound guided IV having all the supplies in one place is essential for placement to be time efficient in the application of medicine or performing blood draws. However, the necessary equipment is often scattered throughout the department or not available in the department, making the procedure even more difficult or impossible to perform. Oftentimes medical professionals resort to using surgical rectal lubrication and attempt to use alcohol swabs on dirty ultrasound probes instead of a sterile sheath.

Ultrasound guided catheters are more often in deeper vessels. This is because vessels closer to the surface are more easily visualized leading to greater success with the conventional technique. With the deep and small nature of the vessels used in the ultrasound guided IV catheter technique it can take more time and attention to place these catheters. More of the catheter is in the soft tissue between the skin surface and the deep vessel, which means that the deeper vessel has less of the catheter within its lumen. A slight slip of the catheter can cause displacement of the catheter from the lumen. In addition, sterile lubrication used for the ultrasound makes it difficult for tape and tegaderm to adhere to the skin. All of these factors make it difficult and essential to secure an ultrasound guided IV catheter.

The placement of an ultrasound guided IV catheter is often painful to the patient. The use of an anesthetic at the skin surface can make catheter placement much more comfortable for the patient. The placing of a catheter via ultrasound usually uses a large bore catheter, 18 gauge or larger. The large gauge is necessary for the rapid transfusion of medicines, fluids and IV contrast, and this can be quite painful, especially because the placement of ultrasound guided IV catheters usually takes longer than the conventional method with a sharp needle being slowly manipulated beneath the skin. The use of local anesthetic at the site of entry can alleviate this pain.

Ultrasound guided catheter introduction kits are currently available for central venous access, but no kits are available for ultrasound guided peripheral venous access.

SUMMARY OF THE INVENTION

Accordingly, it is an object of the invention to provide a needle/catheter introduction apparatus that can be operated with one hand. It is a further object to provide an introduction apparatus that is reliable and easy to use. It is a further object of the invention to provide a catheter that can be visualized with ultrasound. It is yet another object of the invention to provide a probe cover that is easy to use, reliable, and sterile. It is still a further object of the invention to provide an assembly or kit with components needed for ultrasound guided catheter introduction to peripheral veins or arteries.

A needle/catheter introducer is provided that can be operated by one hand. The introducer has a wheel located toward the front end of the device that is rotated by the index finger of the user. After placement of the needle in the lumen of the vessel, the user rotates the wheel, which advances the wire guide through the center of the needle and into the patient. Once the guide wire is advanced into the vessel lumen the catheter can be advanced over the guide wire with a hub or finger tab on the catheter close to the index finger. The introducer fits in the palm of the user's hand and the wheel can be operated by the user's index finger. Because the actions needed to advance the guide wire and advance the catheter can both be comfortably performed by one hand without moving the hand from its initial position, the catheter introducer is easy to use and allows the user to also operate an ultrasound detection device during insertion without the assistance of another person.

In addition, a catheter is provided that is comprised of materials that make the catheter capable of being visualized by ultrasound to enable confirmation of correct placement in a vessel.

In addition, a probe cover is provided that is pre-sterilized and packaged in a cardboard with the top sides of the cover folded down over the cardboard. The cover is placed over the probe end, the sides of the cover are folded up, and the cardboard is removed. The sterile probe cover can be quickly and efficiently placed over the ultrasound's transducer end.

Still further, the invention includes a kit having components needed for ultrasound guided catheter introduction to peripheral veins or arteries. The kit has a sterile package with an ergonomic shape that can be used to stabilize the arm. The needle cover, in addition to protecting the needle, has a tip which can mark the skin to provide a directional marker. This allows the needle to be aligned to the direction of the vessel. The catheter introduction set allows a catheter tube to be introduced into blood vessels such as veins and arteries while keeping the ultrasound probe cover sterile. The introducer assembly is contained in a sterile package, which is designed to be converted into an ergonomic arm stand for assisting in stabilizing the arm while placing the catheter. The sterile package can also contain the sterile probe cover. The introducer assembly is removed as an entire unit including needle, catheter, wire guide, rotational wire guide feed device, needle cover with directional guide. The sterile probe cover is placed on the transducer end of the ultrasound probe. Other items in the kit that one might need to locate separately (outside of peripheral kits) to perform ultrasound guided catheter insertion on peripheral veins or arteries include: lidocaine or other anesthetic, sterile gel (for ultrasound transduction), ultrasound probe cover for sterile patient contact, two rubber bands to secure the ultrasound probe cover, suture material to stabilize the catheter on the arm.

These and other objects of the invention, as well as many of the intended advantages thereof, will become more readily apparent when reference is made to the following description, taken in conjunction with the accompanying drawings.

BRIEF DESCRIPTION OF THE FIGURES

FIG. 19 is a side view of an introducer apparatus in accordance with another embodiment of the invention, without a cover;

FIG. 20 is a perspective cross-sectional view of the introducer of FIG. 19;

DETAILED DESCRIPTION OF THE PREFERRED EMBODIMENTS

Figure 1:
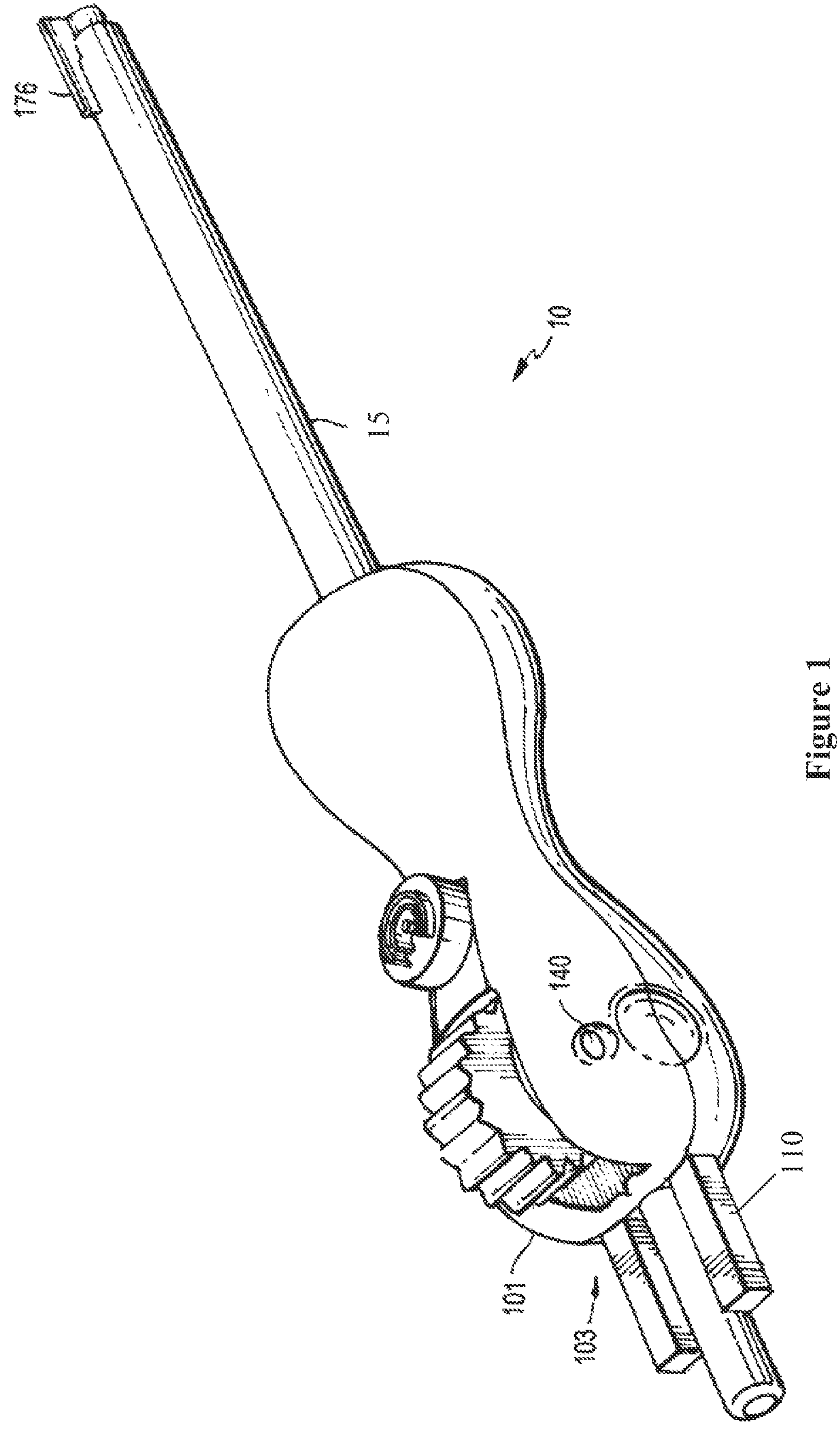
FIG. 1 is a perspective view of the introducer in accordance with the preferred embodiment of the invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. Several preferred embodiments of the invention are described for illustrative purposes, it being understood that the invention may be embodied in other forms not specifically shown in the drawings.

This catheter has several features which will improve medical treatment. With these added features, the catheter makes IV placement with ultrasound easier, more efficient, and more accurate, thus significantly decreasing pain experienced by the patient by reducing the number of IV sticks currently performed.

As shown in the drawings the invention comprises of multiple elements that have separate novel advantages and features, but also can be utilized together to improve medical treatment by making IV placement with ultrasound easier, more efficient and more accurate, and reducing pain. Those elements include a catheter introduction apparatus (FIGS. 1-11B), a UV-visible catheter (FIG. 12), a needle cover with marking means (FIG. 11A-11C), a probe cover (FIGS. 13-15), a sterile kit package (FIGS. 16-18), and a catheter having finger tabs (FIGS. 11A, 11B).

The Introducer Apparatus 10 (FIGS. 1-11)

Figure 2:
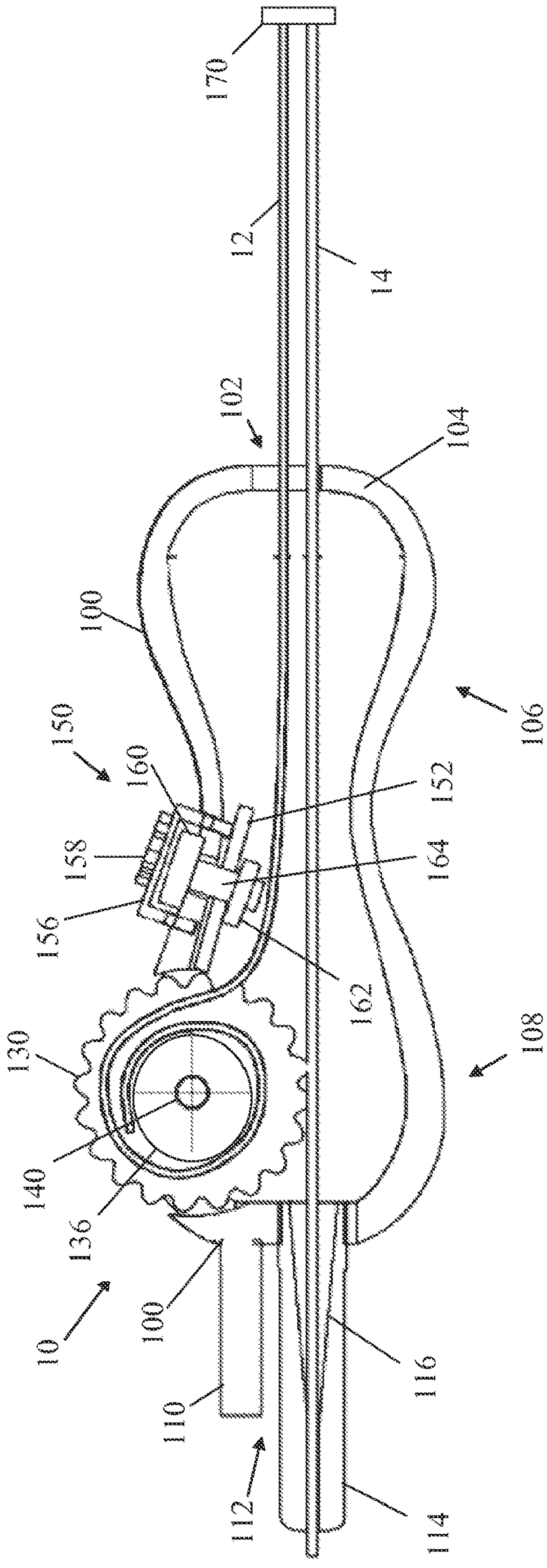
FIG. 2 is a side cross-sectional view of the introducer of FIG. 1.
Figure 3:
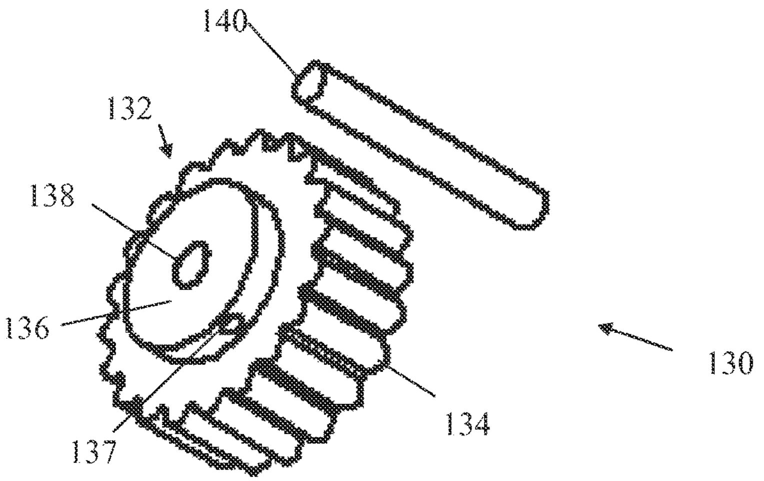
FIG. 3 is an exploded view of the wheel apparatus of FIG. 2.

Turning to FIGS. 1-10, an illustrative non-limiting embodiment of the introducer apparatus 10 is shown. As best shown in FIG. 2, the introducer 10 has a housing 100, wheel assembly 130, drive wire 12, and guide wire 14. The housing 100 is slightly elongated an ergonomically shaped to fit in the palm of a user's hand. The inside of the housing 100 is hollow, such that the housing 100 forms a wall 104. The housing 100 has a front end 108 and a rear end 106. An opening 102 is provided at the rear end 106.

An elongated coupling 114 extends forward from the distal front end 108 of the housing 100. The coupling 114 has the shape of an elongated post having a round cross-section. The coupling 114 has a central opening. At the front of the coupling 114, the central opening is sized to be slightly larger than the guide wire 14. At the middle of the coupling, the opening gets progressively larger to the rear end of the coupling 114. The tapered opening forms guide walls 116 that funnel the guide wire toward the smaller portion of the opening so that the guide wire 14 can be pushed through the coupling 114 and out of the coupling 114 without stubbing or damage.

A guide post 110 is also provided at the front end 108 of the housing 100. The guide post 110 extends forward from the front end 108. The post 110 is elongated, has a square-shaped cross-section (though any suitable shape can be utilized), and extends substantially parallel to and slightly spaced apart from the coupling 114. The post 110 is shorter than the coupling 114, but creates a channel 112 between the post 110 and the coupling 114. An injection needle can then be received over the coupling 14 and is further secured in the channel 110 by the post 110. There can be a single post 110 positioned above the coupling 114 (FIG. 2) or two posts on opposite sides of the coupling 114 (FIG. 1), or both a single post 110 above the coupling and two posts on opposite sides of the coupling. It will be apparent that any number of posts 110 can be provided and positioned anywhere about the coupling 114 to reliably receive and retain the injection needle. In addition, other coupling means can be provided to reliably couple the needle to the housing 100.

As best shown in FIG. 1, the wheel assembly 130 is provided in an opening 103 located at the top of the housing 100 at the front end 108. As more fully shown in FIG. 3, the wheel assembly 130 includes a wheel 132 with teeth 134 that extend transversely along the outer circumferential edge of the wheel 132. The teeth 134 enable the user to more easily turn the wheel 132. A small circular post or drum 136 is provided on one side of the wheel 132. The circular drum 136 projects outward from the side of the wheel 132 and is concentrically aligned with the wheel 132. A through-hole 138 extends transversely through the center of the drum 136 and the wheel 132. A pin 140 extends through the through-hole 138 and engages openings in the two opposing sides 101 (FIG. 1) of the housing 100 so that the wheel 132 can rotate about the pin 130. The drum 136 is fixed to the wheel 132 so that the drum 136 rotates as the wheel 132 rotates.

Returning to FIG. 2, one end of the drive wire 12 is partly wrapped about the drum 136. For instance, the distal end of the drive wire 12 can be at least partially placed in a hole 137 (FIG. 3) that extends at least part way through the drum 136 to hold the drive wire 12 in place on the drum 136. Other suitable coupling methods can be used, such as adhesive, or a fastener. Thus, the user can wind the drive wire 12 to retract the drive wire 12. The drive wire 12 is sufficiently rigid to retain a straight form, but sufficiently flexible to wind about the drum 136 of the wheel 132.

Still referring to FIG. 2, a lock assembly 150 is located just behind the wheel assembly 130 on the housing 100. The lock assembly 150 includes a locking tab 152, cover 156, nut 162, bolt 164, and display area 158 that can be used to present a logo or directions to the user. The bolt 164 extends through an opening in the housing 100 and an opening in the locking tab 152. The head 160 of the bolt 164 is outside of the housing 100 and the bolt 164 attaches to a nut 162 located on the opposite side of the locking tab 152. The bolt 164 fastens the tab 152 in place on the housing 100 to engage the teeth 134 of the wheel 132. The locking tab 152 is a flat element that extends to the teeth 134 on the wheel 132. The tab 152 can be somewhat flexible, so that the user can operate the wheel 132. However, the tab 152 prevents the wheel 132 from moving when not be operated on by the user, and in particular prevents the wheel 132 from moving backwards to retract the drive wire 14. The tab 152 can also make a clicking noise as the wheel 132 is being moved forward, to provide an audible and/or tactile feedback that confirms to the user that the wheel 132 is being moved. Though a bolt and tab 152 are shown, it will be readily apparent that other mechanisms can be provided to prevent unintended operation of the wheel 132. For instance, the wheel 132 can be friction fit into the opening 103 so that a slight force is needed to move the wheel 132. The cover 156 extends over the bolt head 160 so that the user does not get injured by the bolt head 160. The cover 156 can be adhered or fastened to the housing 100.

Figure 4:
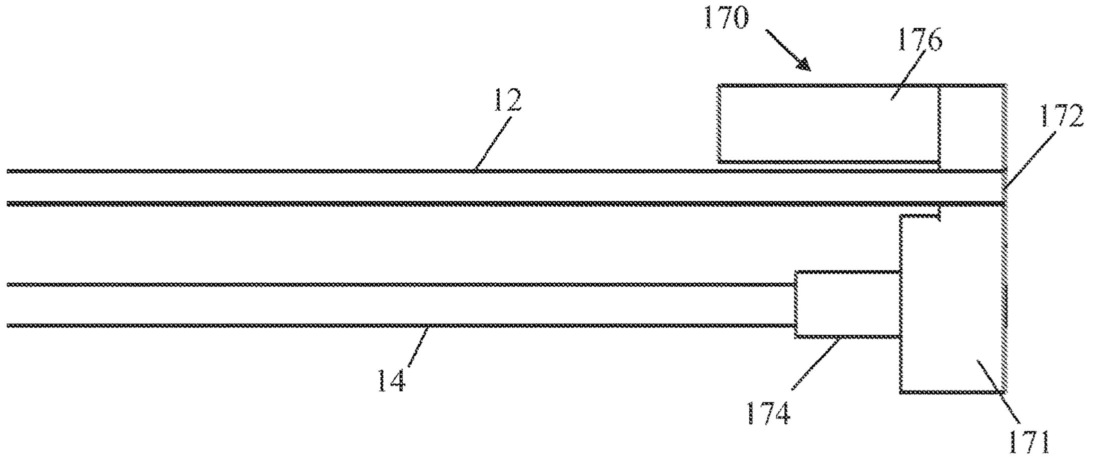
FIG. 4 is a side view of the wire connector used to couple the drive wire to the guide wire in FIG. 1.

A connector or plug 170 is provided at the distal ends of the drive wire 12 and the guide wire 14. As best shown in FIG. 4, the connector 170 is configured to engage both the drive wire 12 and the guide wire 14 so that the guide wire 14 moves when the drive wire 14 moves. The connector 170 has a connector body 171 that includes a first opening 172 that receives the drive wire 12 by a friction fit. The body 171 also has a post 174 that extends forward and has an opening that receives the guide wire 14 by a friction fit. In addition, the body 171 includes a guide post or guide tab 176 that extends forward substantially parallel to the drive wire 12. A small channel is formed between the tab 176 and the drive wire 12 to receive and engage a tube or sheath 15 (FIG. 1) that surrounds the two wires 12, 14 to prevent injury to the user or patient. A slit extends the entire longitudinal length of the sheath 15, and the guide post 176 moves through the slit. This keeps the drive wire 12 and the guide wire 14 properly oriented with respect to each other during operation and so they do not become twisted. Instead of a sheath 15, the housing 100 can be extended to cover the two wires 12, 14.

Operation of the introducer 10 will now be discussed with respect to FIGS. 5-9. In these illustrative non-limiting embodiments, the introducer 10 is coupled with a conventional introducer needle assembly 200 having a standard catheter. One example of a suitable needle assembly is offered by Smiths-Medical, JELCO® I.V. Catheter, http://www.smiths-medical.com/catalog/peripheral-catheters/conventional-catheters/jelco-conventional-catheters/jelco-v-catheter-radiopaque.html. It will be recognized however, that the introducer 10 can be used with other suitable devices, such as Insyte™ Autoguard™ Shielded IV Catheters by Becton Dickinson (http://www.medline.com/product/Insyte153-Autoguard153-Shielded-IV-Catheters-by-Becton-Dickinson/IV-Catheters/Z05-PF29088#.UwqiYfldWo0), Introcan Safety® IV Catheter Straight by B Braun (http://www.medline.com/product/Introcan-Safety-IV-Catheter-Straight-by-B-Braun/IV-Catheters/Z05-PF70731#.UwqiufldWo0), IV Catheters by Exel International (http://www.medline.com/product/IV-Catheters-by-Exel-International/IV-Catheters/Z05-PF29139#.Uwqi-vldWo0), and OPTIVA® IV Catheters by Smiths Medical (http://www.medline.com/product/OPTIVA-IV-Catheters-by-Smiths-Medical/IV-Catheters/Z05-PF52843#.UwqjavldWo0).

Figure 5:
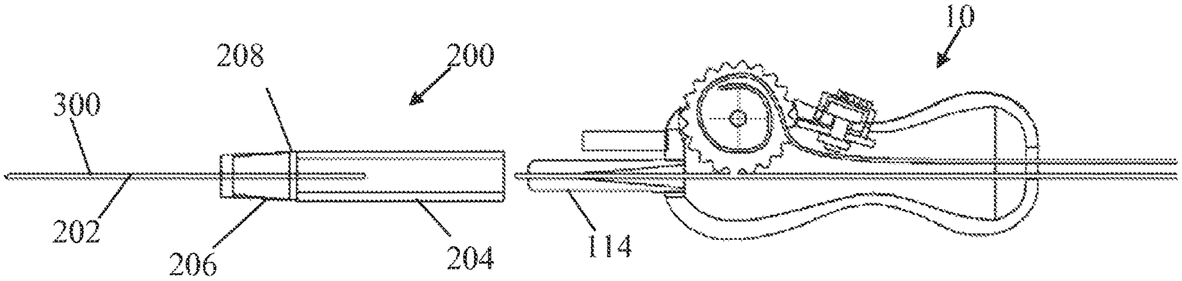
FIG. 5 is a side cross-sectional view of the introducer just prior to a needle being placed on the introducer.

As shown in FIG. 5, the needle assembly 200 has a round tubular housing 204, needle 202, hub 206 and support member 208. The housing 204 has a first end that is open and mates with the coupling member 114. The support member 208 is fitted at an opposite end of the needle housing 204 and the hub 206 is placed about the support member 208. The needle 202 extends through openings in the hub 206 and support member 208 and partly into the front end of the interior of the housing 204. The coupling 114 of the introducer assembly 10 aligns the guide wire 14 with the needle 202 of the needle assembly 200. A catheter 300 extends over the outside of the needle 202 and terminates at and couples with the hub 206.

Figure 6:
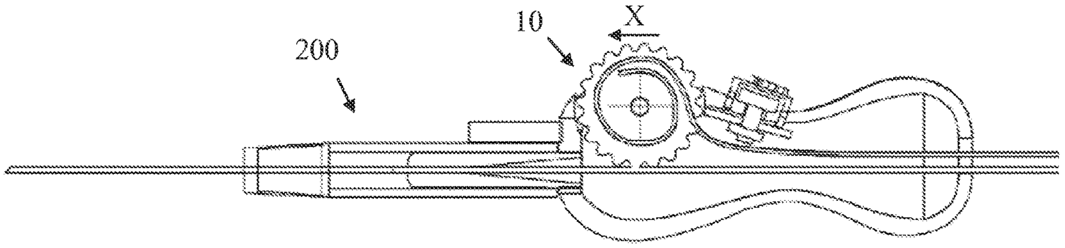
FIG. 6 is a side cross-sectional view of the introducer coupled with the needle.

The operation starts with FIG. 5, where a needle assembly 200 is aligned with the introducer 10. The drive wire 12 and guide wire 14 are fully retracted at the rear of the introducer 10. Turning now to FIG. 6, the user places the needle assembly 200 on the introducer 10. The tubular housing 204 of the needle assembly 200 is slidably received over the coupling 114 of the introducer 10. The housing 204 wall enters the channel(s) 112 between the one or more post(s) 110 and the coupling 114. The needle housing 204 fits snugly about the coupling 114, so that the needle assembly 200 does not come free of the introducer 10 until operated on by the user. As shown, the guide wire 14 is aligned with the needle 202. It will be appreciated that though this is described as a manual process, the introducer 10 can come pre-loaded with a needle assembly 200 already positioned on the introducer 10. Or the introducer 10 can have a needle integrally formed with the introducer 10.

At this point the user places the needle 202 into the patient, such as the vein or artery lumen. To do so, the needle cover 250 (FIG. 11B) is first taken off of the needle and the needle cover tip 252 (FIGS. 11B, 11C) is used to mark the skin surface either with pressure or a marking ink in two spots to give directional marking for the direction of the cannulation. The needle cover tip 252 has one or more projections 254 that extend forward from the front surface of the tip 252. The projections 254 shown are concentric curves that form a company logo. However, the projection(s) 254 can have any shape, such as an arrow, line, or dot. Ink can be placed on the projections 254 and applied to the patient. Or, the projections 254 can be pushed into the patient's skin without ink, to cause pressure indentations on the patient. The user can use the inked cap to place directional markings on the patient. Without this it can be difficult to place cannula once it has entered under the skin. This can be especially useful with ultrasound guidance. Both marks are made at points along the vessel. The cannula (also called a catheter) 300 is placed in the direction of this guidance in line with the vessel and the needle 202 is inserted into the patient. For deep vessels and small vessels the directional marking is of particular advantage. To visualize smaller vessels ultrasound can be used. As further shown in FIG. 11B, the needle cover 250 has a main tube that extends the length of the needle 202, and one or more arms 256 at the rear end that extend outward and upward over the top of the hub 206. The arms 256 protect the hub 206 and make it easy for the user to remove the cover 250. The cover 250 can come pre-assembled over the needle 202, and protects the user from being injured by the needle 202.

Returning to FIG. 6, after the needle cover 250 is removed, the needle is aligned along the skin with the two points marked for direction and then inserted into the lumen of the vessel. Once the needle 202 is proper placed, the user turns the wheel 132 forward with an index finger in the direction X. This operation can be done using a single hand of the user. Since the needle 202 is already positioned in the vein, the user simply rotates the wheel 132, which is easy to reach because it is at the front end 108 of the housing body 100. Thus, the user can retain hold of the housing 100 in the palm of the hand and (without moving his hand) operate the wheel 132 with the index finger. In addition, the user holds the introducer 10 steady (i.e., it does not have to be moved forward) and allows the movement of the wheel 132 to advance the guide wire 12, so that single-handed operation is possible. Single-handed operation is further made possible by the contour shape of the hub. Thus, the user can hold an ultrasound probe in the other hand to assist placement of the guide wire 12 and catheter 300. The tab 152 prevents the wheel 132 from moving in reverse.

Figure 7:
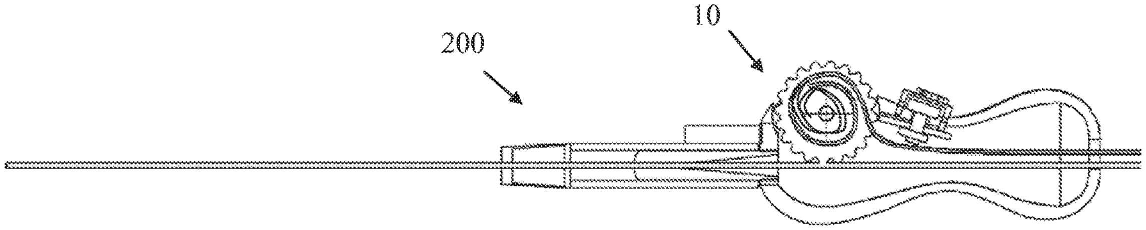
FIG. 7 is a side cross-sectional view of the introducer with the guide wire extended.

As the wheel 132 is moved forward, it draws the drive wire 12 further onto and around the wheel drum 136. This, in turn, causes the connector 170 to push the guide wire 14 forward (to the left in the embodiment of FIG. 7). The guide wire 14 enters the central opening in the needle 202 and continues through the needle 202 until it emerges from the distal tip of the needle 202 and enters the patient, as shown in FIG. 7. Accordingly, the guide wire 14 threads the vessel lumen.

Figure 8:
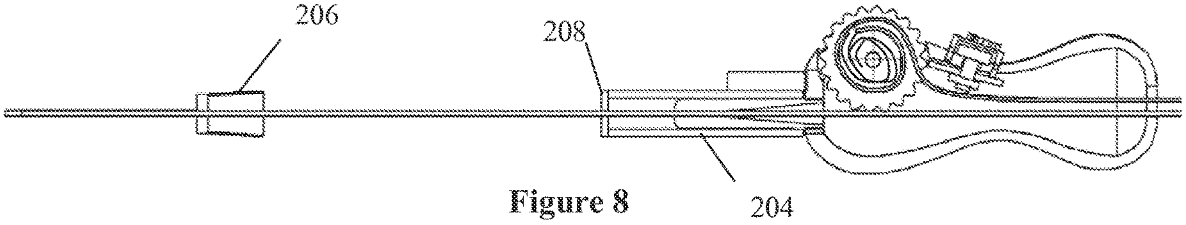
FIG. 8 shows the hub extended forward on the guide wire.
Figure 9:
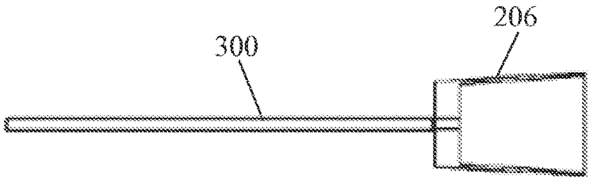
FIG. 9 shows the hub and catheter that remains in a patient's body following removal of the introducer and introducer needle.

The thin guide wire 14 is then ready to have the soft plastic catheter 300 slid over the guide wire 14 into the vessel lumen. As shown in FIG. 8, once the guide wire 14 has entered the user's vein (which is roughly one to two and a half inches depending on catheter length), the user pushes the hub 206 (or finger tabs on the catheter 300, if used) forward to force the catheter off the needle 202 and into the patient. The support 208 keeps the needle 202 positioned on the introducer 10. The catheter 300 can be pushed into the patient further than the needle 202 and/or guide wire 12 since it is more flexible and won't puncture the side of the vein or vessel. The user can then remove the needle 202 and guide wire 12 from the patient, leaving the catheter and hub 206 properly placed in the patient, as shown in FIG. 9. The user can then connect a syringe, intra venous (IV) device or other medical instrument at the rear end of the hub 206.

Figure 10A:
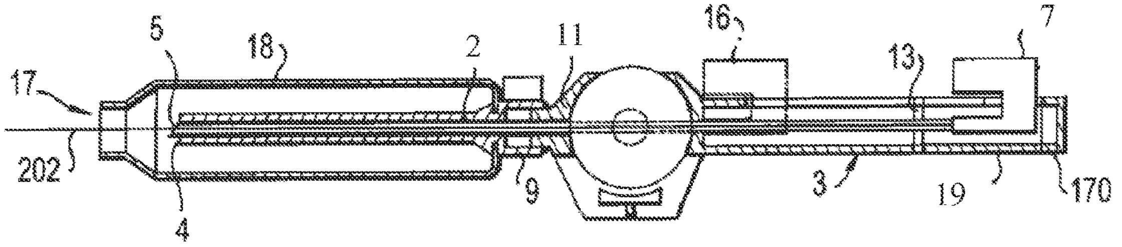
FIG. 10A is an alternative embodiment of the introducer.
Figure 11A:
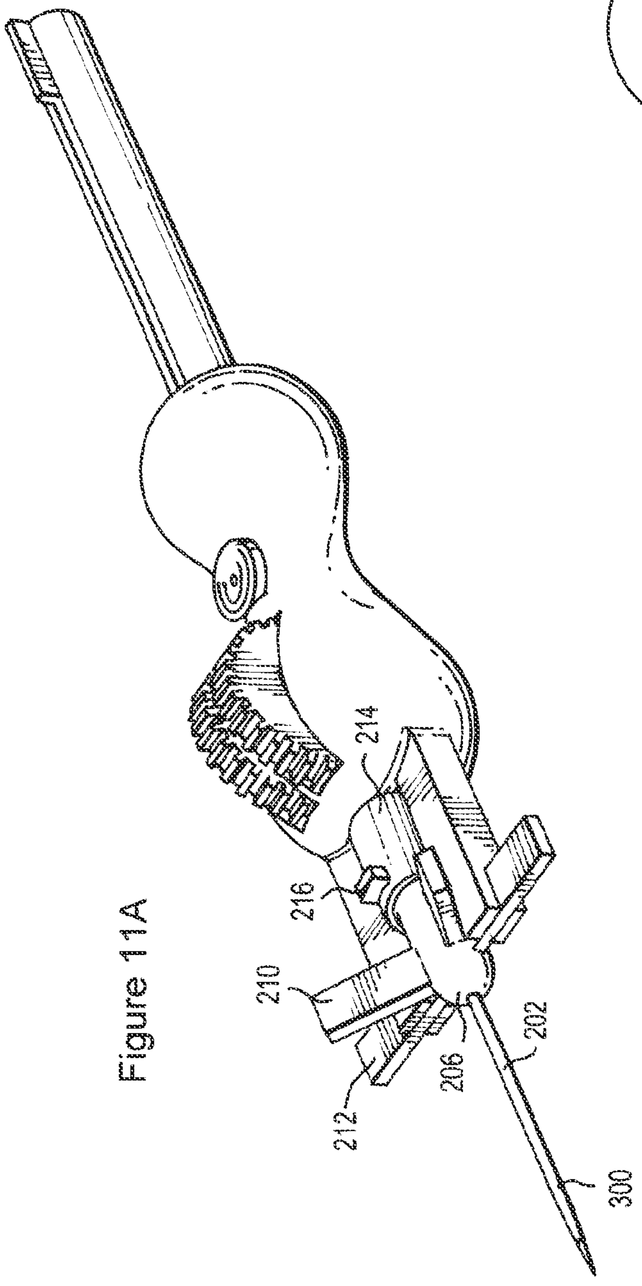
FIG. 11A is a perspective view of the introducer device having needle handles and hub handles with the two-wheel assembly of FIG. 10B.
Figure 11B:
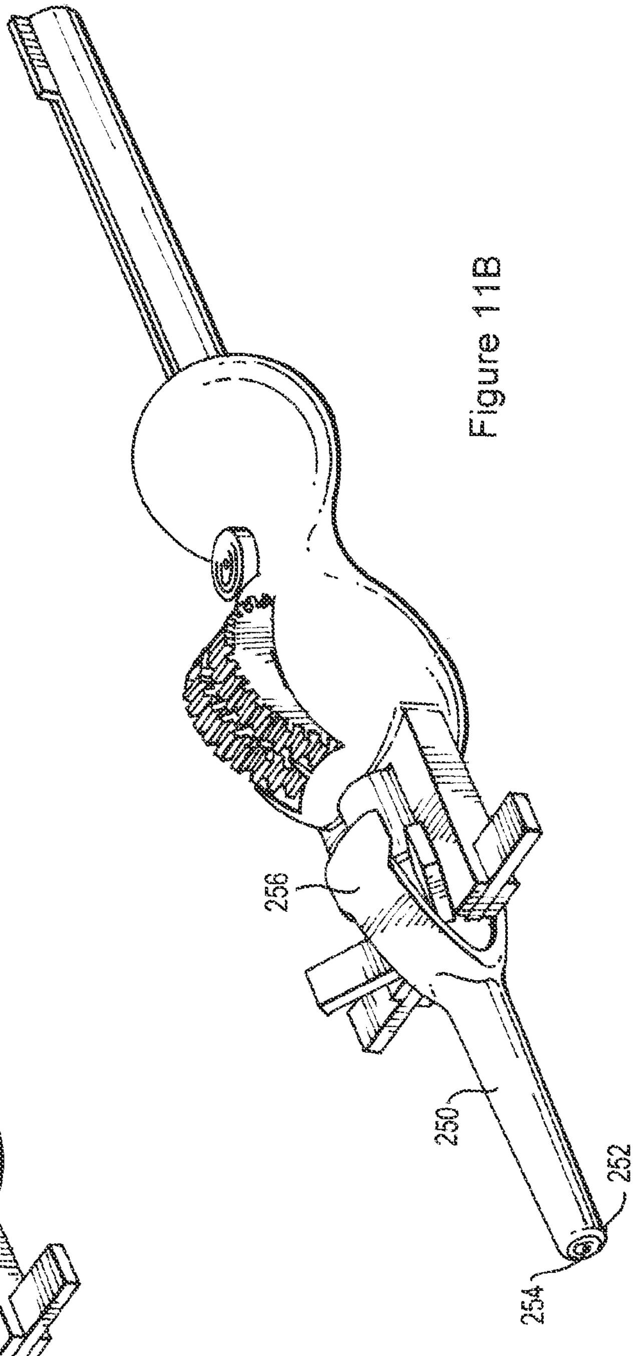
FIG. 11B is a perspective view of the introducer device of FIG. 11A having a needle cover.
Figure 11C:
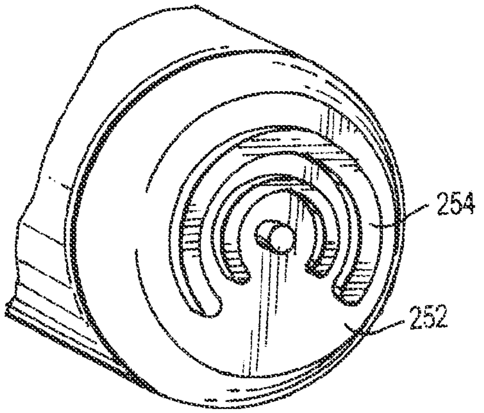
FIG. 11C is a detailed view of the needle cover tip having projections.

Turning to FIG. 10A, an alternative embodiment of the invention is shown. Here, the needle 202 is an elongated shank portion having a beveled tip. The shank is hollow or canullated and is joined at its rear or end to a hollow transparent hub 2 having a rounded front end. The catheter 300 is sized to be telescopically fitted over the shank of the needle 202. As with FIGS. 1-9, the catheter 300 is slightly shorter than the needle 202 so that when it is fully pushed back against the needle hub 2 the beveled tip 5 of the needle projects outwardly from the catheter tip 4 by an amount sufficient to permit puncture of the blood vessel by the user of the device. A female luer-type fitting 9 is formed on the rear of the catheter and mates with and fits over a shoulder projection 11 on the front of the hub 2. The wire guide assembly 3 includes an elongated tubular member 19 which is fitted into the counter bore at the end of hub 2. The tubular member 19 can be formed of a transparent, semi-rigid plastic material, and have sufficient resilience to maintains its tubular configuration and use. A guidance tab 16 interfaces with the hollow, grooved tube 19. The tab 16 is attached to the back of the guide wire, and slides through the groove, making sure that the wire does not tangle or twist. The shoulder projection 11 is a solid plastic piece that is part of the housing and holds the wheel. A flash guard 13 keeps blood from spilling or squirting out the back end of the device. A safety cap 18 is also provided that can be removed when the device is used.

In its preferred form, the tubular member 19 has a longitudinally extending slot running from a point adjacent the needle hub 2. A plug or other suitable sealing means provides a seal for the end. An elongated flexible spring wire guide is housed within tubular member 19. A wheel is provided that directly acts on the spring wire guide to advance the spring wire guide. This can be done, for instance, by a drum or shaft that is attached to the wheel. The outer surface of the drum can press the guide wire between a fixed surface on the housing to physically move the guide wire forward by friction. The drum can have a surface that grabs the guide wire.

A laterally or radially extending handle 7 is fastened to its rear end handle projects through the slot and is adapted to advance the spring wire guide through the lumen through needle and outwardly from the distal end into and through the lumen of the blood vessel. For facilitating this insertion with the use of one hand the index finger pushes one of the finger tabs on either side of the cannula 4. Once in place the cannula 4 can be secured with the securing tabs. The securing tabs can be secured to the skin, either with an adhesive tape or sutured into place through the holes in these tabs.

The tabs 210 are best shown in FIG. 11A. The needle 202 is connected to a hub 206 having a rounded front end. Handles or tabs 212 are connected to the catheter, and handles or tabs 210 are connected to the hub 206. The catheter handles 212 and the hub handles 210 are elongated and rectangular, and extend outward substantially transverse to the catheter 300 and hub 206, respectively. The user can grab the tabs 202 to push the catheter 300 forward. And the user can grab the tabs 210 to push the hub 206 forward. Thus, the hub 206 has elongated slots to receive the hub handles 210. The catheter handles 212 and the hub handles 210 are easier for the user to grab and operate.

As further shown in FIG. 11A, a flash chamber 214 can be provided behind the hub 206. The flash chamber 214 allows the user to see blood and fluid. Once the vessel is pierced by the needle 202, blood enters the flash chamber 214. The flash chamber 214 is transparent, so that the user can visually confirm that the vessel has been pierced but to keep the blood from getting on the practitioner, patient or device. The chamber 214 has a tab 216 that can connect to a safety cap. In the present embodiment, the needle 202 is connected to the flash chamber 214, but the flash chamber 214 is not connected with the hub 206. The catheter 300 is connected to the hub 206.

Figure 10B:
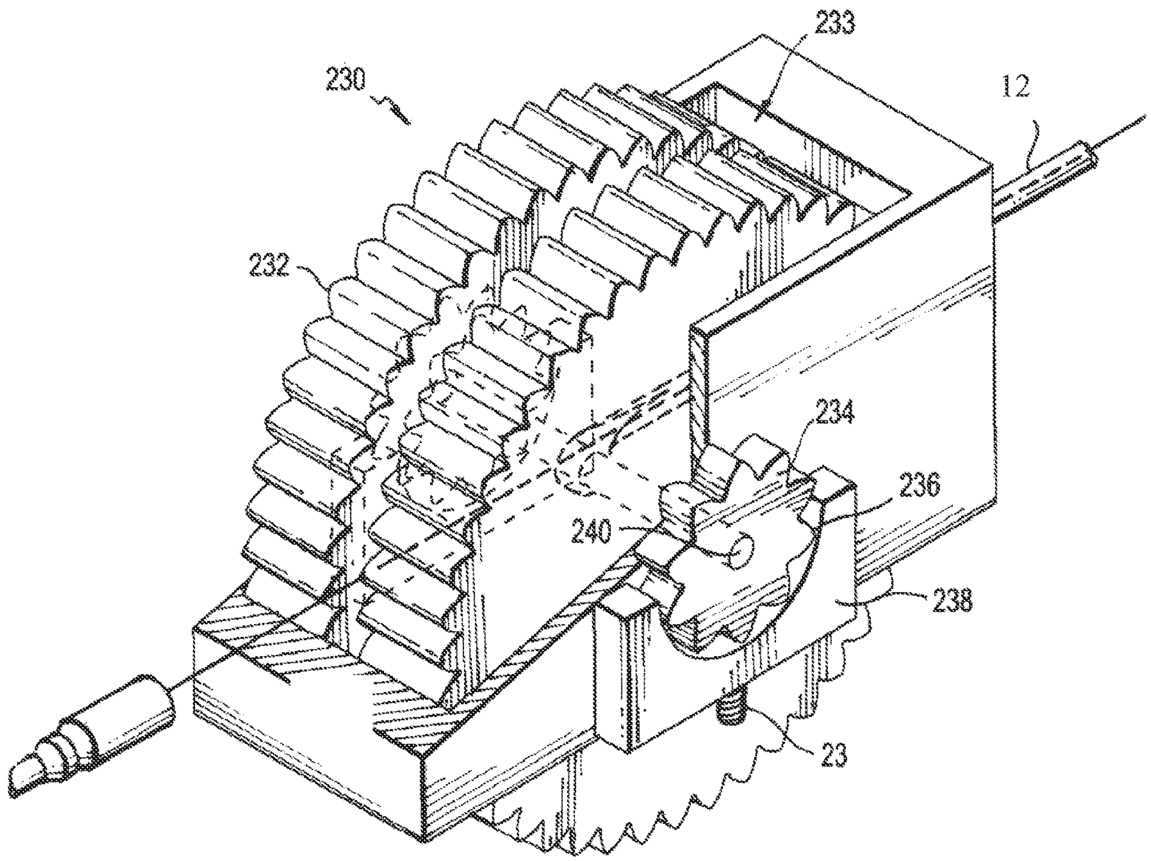
FIG. 10B is a perspective view of the wheel assembly in accordance with an alternative embodiment of the invention.

Turning to FIG. 10B, an alternative embodiment of the wheel assembly of FIGS. 1-9 is shown. Here, the wheel assembly 230 has two wheels 232 separated from each other by a slight gap 233. The wheels 232 have an outer circumferential edge that can have transverse ridges, a roughened surface or an easy to grip surface (such as rubber), to make it easy for the user to operate the wheels 232. A circular drum 234 is affixed to or integral with the side of one of the wheels 232. The drum 234 has an outer circumferential edge with large transverse ridges or teeth 236 positioned thereabout. A locking structure 238 is coupled to the housing 100 of the introducer 10 and aligned with the drum 234. The locking structure 238 has a top inner surface that is aligned with the drum 234, and can optionally include at least one mating tooth that engages the drum teeth 236. The drum teeth 236 are configured so that the wheel 232 can advance the guide wire 14 into the patient, but that the wheel 232 cannot be reversed. The inner surface of the locking structure 238 can also rub against the surface of the teeth 236 so that the wheel 232 does not move without being operated on by the user. A pin 240 extends through the center of the wheels 232 and drum 234 to permit the wheels 232 and pin 240 to rotate with respect to the housing 100. The drive wire 12 extends into the gap 233 between the wheels 232 and the end of the drive wire 12 is wrapped about the pin 240. Thus, as the user operates the wheels 232, the drive wire 12 wraps around the pin 240 and advances the guide wire 14 into the patient. The pin 240 can optionally have a widened portion at the gap 233 to receive the drive wire 12. Or, the two wheels 232 can be connected together as a single wheel that has a channel which receives the drive wire 12, and the pin 240 need not move. It will be apparent that other suitable configurations can be provided within the spirit and scope of the invention.

Usually the wire guide 12 only needs to be fed forward, so the default state of the wire guide feed wheel assembly prevents backward feeding. To prevent backward feeding, the tab 152 (FIG. 2) or gear box 238 (FIG. 10B) unidirectional block movement of the drum teeth 236. In order to allow backward feeding of the wire guide, a user can unscrew the bolt 164 (FIG. 2) or push down on the wheels 232 (FIG. 10B) and rotate the wheels 232 in the direction opposite of that for forward feeding. Pushing down on the wheels 232 moves the drum 234 away from the gear box 238, enabling backward rotation. A spring 23 can maintain the drum teeth 236 in contact with the gear box teeth in the default setting.

The entire introducer 10 can be made of a plastic (e.g., medical grade polymers and UV cure adhesives), except that the tab 152, bolt 164, nut 162, drive wire 12 and guide wire 14 are preferably made of metal (such as stainless steel, 300 series). The entire introducer can be sterilized and packaged in a sterilized container, such as being heat sealed in a plastic bag. A typical material for the catheter is Tecoflex EG-80A polyurethane. Component materials are usually a polycarbonate like Lexan HP4 or an ABS like Cycolac HMG47MD.

In a non-limiting illustrative embodiment of the invention, the coupling element 114 is about 1 cm long with a diameter of about 4 mm. The introducer 10 is about 6.2 cm long (including the coupling element 114), and has a width of about 3.8 mm. The wheel 132 has a diameter of about 1.4 cm. The drive wire 12 has a length of about 20-29 cm, and the guide wire 14 has a length of about 18-27 cm so that the guide wire 14 can be advanced through the longest needle that is used. The coupling 114 can be sized to fit any needle, and the guide wire 14 can be sized to any size needle. Common size needles are 16-18 gauge, but larger gauges such as 14-15 would be suitable, and still larger or smaller needles may be suitable as well.

The Ultrasound-Guided IV Catheter has a number of features that make placement of the catheter in deep peripheral vessels easier. First, it has an inked cap that permits the user to mark the location and direction of the vessel as visualized by the ultrasound machine. This gives directional guidance to the catheter along the vessel for insertion. The cap can mark the skin for directional guidance. When placing an ultrasound guided IV catheter the medical professional placing that catheter can get lost as to the direction of the needle in relationship to the vessel. The Ultrasound gives a two dimensional image which does not show direction. The cap on the ultrasound guided IV marks the surface of the skin so the direction of the vessel can be marked on the skin. For instance, the marking can have an ink spot or directional arrow indention into the skin, allowing the catheter to be aligned to the vessel. The medical professional can then align the needle/catheter which the markings and not miss the vessel.

Second, the catheter has a slender guide-wire that can easily thread smaller, deeper vessels. The guide-wire can easily thread deep vessels and advance the catheter without catching on the vessel walls. The ultrasound is used to find deeper vessels which cannot be visualized by the human eye. These deep vessels are difficult to thread with the soft large plastic catheters. The catheter can catch on the sides of the vessel and thus not slide easily into the lumen of the vessel. The Ultrasound guided IV catheter uses a thin guide wire to thread deep vessels. The guide-wire is placed within the lumen of the vessel first and then the catheter is threaded over the catheter, preventing the catheter from getting caught on the sides of the vessel wall.

The guide-wire and catheter can be advanced and placed with only one hand so that as one holds the catheter with one hand the other hand holds the ultrasound and visualizes correct entry into the vessel. The drive wheel advances the guide wire 14, and the catheter tabs or hub advance catheter over the guide-wire. The other hand is free to manipulate the ultrasound. When moving the guide-wire into the vessel a traditional catheter needs two hands for guide-wire placement: one hand placing the catheter and the other hand advancing the guide wire. The Ultrasound guided IV catheter advances the guide-wire and catheter with the same hand. This gives a unique advantage to ultrasound guidance because one person can use his spare hand to hold the ultrasound to visualize the guide-wire and catheter being advance ensuring placement in the vessel lumen.

The present introducer avoids potential complications with exposure to blood and fluid, and provides a tactile resistance. The drive wire also provides a spring-like behavior when wound about the wheel assembly to provide greater control of the advancement and retraction of the drive wire. However, it will be apparent that other configurations of the introducer may be possible within the spirit and scope of the invention. For instance, the drive wire can be eliminated and the guide wire directly connected to the wheel assembly to push the guide wire.

The Introducer Apparatus 600 (FIGS. 19- 23)

Turning to FIGS. 19-23, an introducer apparatus 600 is shown in accordance with another embodiment of the invention. The apparatus 600 generally includes a housing 602, a drive wheel assembly 610, one or more retainer assemblies 640, 650, 660, and a leaf spring assembly 620.

The housing 602 includes a front end housing 604 and a rear end housing 606. The rear end 606 of the housing 602 has a curved ergonomic shape to be easily grasped and held by a user with the palm about the rear end housing 606 and the finger (such as the index finger) or thumb resting on or about the guide wheel assembly 610. The housing 602 has an internal space that houses the components and protects the user from interfering with the operation of those components or being injured.

Figure 21:
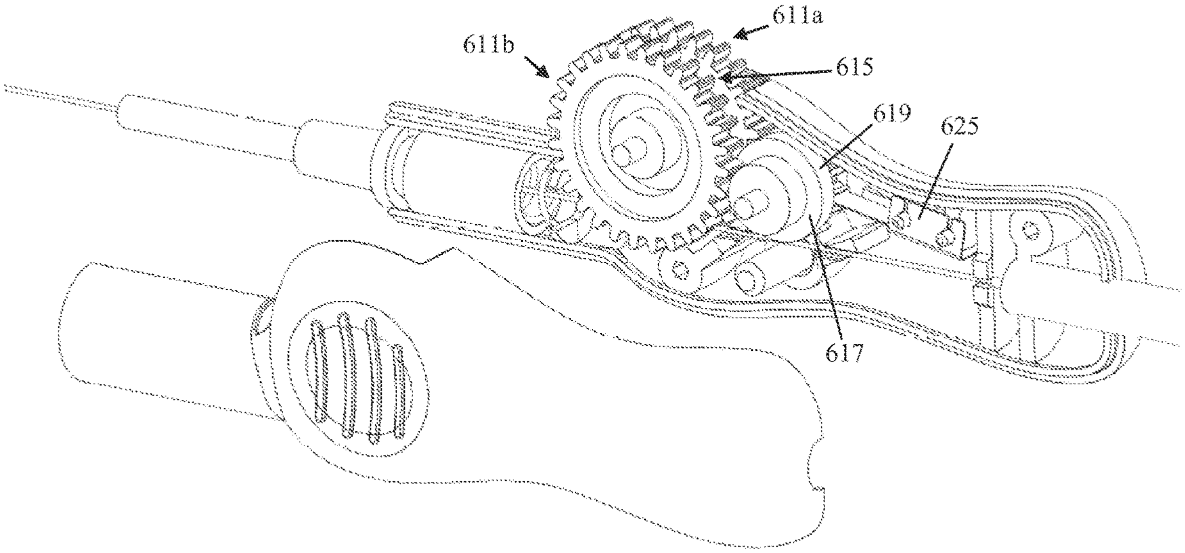
FIG. 21 is a perspective view of the introducer of FIG. 19, with the cover shown separate.

As best shown in FIG. 21, the drive wheel assembly 610 has two drive wheels 611*a*, 611*b* and a spacer plate 613 (FIG. 20). The drive wheel assembly 610 is positioned at an opening formed at the front end 604 of the housing 602 and extends to a top of the housing 602. The drive wheel assembly 610 is aligned so that it rotates in a direction Y (FIG. 20) that is parallel to the longitudinal axis of the apparatus 600. The drive wheel assembly 610 can be centered with respect to the width of the housing 602 so that the drive wheel assembly 610 is aligned with the central longitudinal axis of the apparatus 600. Thus, the drive wheel assembly 610 has two wheels 611 that can be rotated by the user in the direction Y, which is toward the forward end 602 and away from the user. The drive wheels 611 each have a number of teeth 612 positioned along its outer circumference, with channels 614 formed between the teeth 612. The teeth 612 provide a tactile response and friction for the user to better rotate the drive wheels 611. The outer edges of the teeth 612 are slightly rounded so that they are comfortable to push by the user, and can be coated with a rubber or other material that enhances the user's ability to grip the teeth 612 with a finger or thumb.

The spacer plate 613 (FIG. 20) extends outward from the inward-facing side of a first wheel 611*a*. The spacing plate 613 defines a space or gap 615 (FIG. 21) between the two wheels 611*a,* 611*b* having a certain distance sufficient to permit the guide wire 603 to pass between the two wheels 611*a,* 611*b* unobstructed. Accordingly, the plate 613 is wider than the diameter of the guide wire 603. And, the spacer plate 613 has an outer diameter that is smaller than the outer diameter of the wheels 611, so that the gap 615 is formed and the guide wire 603 can pass between the two wheels 611*a,* 611*b*. The two wheels 611*a,* 611*b* can be separate from one another, as shown. Alternatively, the wheel assembly 610 can be a single integral piece, whereby the two wheels 611*a,* 611*b* are integrally formed with the center spacer plate 613. Still further, the wheel assembly 610 need not have two wheels 611*a,* 611*b* and a spacer plate 613, but can have a single wheel and the guide wire 603 can pass to the side of the single wheel. In addition, while the wheel assembly 610 is described as having two wheels 611*a,* 611*b* and a spacer plate 613, it can also be described as a single integral wheel having a central channel 615.

A drive wheel 616 is provided adjacent to the guide wheel assembly 610. As shown in FIG. 20, the drive wheel 616 has teeth 618 and a wheel plate 617 and is formed as a single integral member. The teeth 618 interlock with and cooperatively engage the teeth 612 of the first guide wheel 611*a*. Accordingly, when the user rotates the drive wheel 611*a,* the guide wheel teeth 612 operate the drive wheel teeth 618 to rotate the drive wheel 616. The wheel plate 617 has an outer facing surface extending about the outer circumference of the plate 617. A rubber gasket 619 is positioned about the outer surface (or the outer surface can be made of rubber or coated with a rubber material). The outer surface or rubber gasket 619 contacts and thereby engages the guide wire 603. The rubber material of the rubber gasket 619 grips the guide wire 603 so that when the drive wheel 616 moves, the rubber gasket 619 pushes the guide wire 603 forward (to the left in the embodiment of FIGS. 20, 21) out of the apparatus 600. Thus, the guide wire 603 moves in the same direction Y that the user moves the guide wheel 610.

As shown in FIG. 21, each the guide wheel 610 and the drive wheel 606 are each rotatably mounted to the interior sides of the housing 602 by a pin. The pins are fixed to or formed at the outer-facing side of the wheels 611*a,* 611*b,* and both outer-facing sides of the drive wheel 616 and extend transversely outward with respect to the outer-facing sides of the wheels 611*a,* 611*b,* 616. The pins are received in mating circular openings formed in the sides of the housing 602. For instance, the channels can be formed directly in the side of the housing, or formed in a support member that projects outward from the side (inward with respect to the housing). The pins rotate within the circular openings so that the wheel assembly 610 and the drive wheel 606 can freely rotate with respect to the housing 602.

A leaf spring assembly 620 is provided adjacent the drive wheel 616. The leaf spring assembly 620 has a bracket 625 and a leaf spring 628. The bracket 625 attaches the assembly 620 to the inside of the housing 602. The leaf spring 628 is an elongated and thin piece of metal. The leaf spring 628 extends from the bracket 625 toward the drive wheel 616. As shown in FIGS. 20, 21, the leaf spring 628 is aligned with the drive wheel teeth 618 and the distal end of the leaf spring 628 extends into the channels between the drive wheel teeth 618. The leaf spring 628 is rigid, such as steel, but is thin and narrow so that the spring 628 moves from channel to channel between the teeth as the drive wheel 616 advances. That action provides an auditory click and a tactile measure of movement. The spring 628 can be formed integral with the bracket 625 and bent at a right angle so that the bracket 625 can be screwed to posts 622 that extend from the side and/or top of the housing 602, as shown. Spring mounts 626 can be provided that keep the spring 628 properly positioned and support the spring 628. The mount 626 has a groove that receives the spring 628.

In addition, the spring 628 can be utilized to prevent backward motion of the guide wire 603. The natural stiffness of the spring 628 material (and/or curvature of the spring 628) prevents the spring 628 from bending in a backward direction, which in turn prevents backward movement of the drive wheel 616 by preventing the teeth 618 from moving in reverse beyond the spring 628. Thus, the user cannot inadvertently rotate the guide wheel assembly in a reverse direction to the forward direction Y, since the spring 628 prevents that operation via its interaction with the drive wheel 616. It is noted, however, that the drive wheel 616 is not under tension from a drive wire (since there is no drive wire), so there is no tension on the guide wire 603 to move in reverse.

The retainer or guide assemblies 630, 640, 650, 660 are positioned along the length of the guide wire 603 inside the housing 602. The guide assemblies 630, 640, 650, 660 have arms that form ribs 634, 644, 654, 664, respectively. The guide ribs 634, 644, 654, 664 extend about the guide wire 603 and provide support for the guide wire 603 at various points in the housing 603 to keep the guide wire 603 from slipping or moving off of the drive assembly 616. For instance, the rib 634 extends entirely around the sheath 601 to support the sheath 601 and the wire 603 inside the sheath 601, and hold them in place. The rib 644 can be positioned near the sheath 601 and extend completely around the wire 603 with the wire 603 extending through an opening in the rib 644. The rib 654 can be to both the sides (with one rib 654 shown to one side) of the guide wire 603, and the rib 664 can be beneath the wire 603. The ribs 634, 644, 654, 664 can be made of polycarbonate, polyeurethane or ABS. The ribs can be are molded features of the housing, and not separate pieces.

In addition, a contact peg 652 can be provided to hold the guide wire 603 in place against the drive wheel 616 and gasket 619. As best shown in FIG. 20, the peg 652 can be provided at the top of the post that holds the rib 654. The peg 652 is aligned with the drive wheel 617, so that the guide wire 603 is positioned between the drive wheel gasket 619 and the outer circumferential surface of the peg 652. The peg 652 can be rotatably mounted to at the top of the post so that the peg 652 rotates as the guide wire 603 moves. The outer surface of the peg 652 can be made of or coated with rubber material or have a rubber gasket. The peg 652 is positioned between two posts that are respectively coupled with the sides of the housing, though only one post is shown on the housing halves in the embodiments of FIGS. 20-21. The peg 652 and drive wheel 616 prevent the guide wire 603 from moving up/down in the embodiments shown, and the ribs 654, 664 prevent the guide wire 603 from moving in/out of the apparatus in the embodiments shown. Any suitable number of ribs and pegs can be provided, having any suitable shape, to keep the guide wire 603 properly positioned.

The front end housing 604 extends forward from the rear housing 606. The front housing 604 is generally tubular. A support plate 696 (FIG. 20) is provided at the back side of the front end housing 604. The support plate 696 has a central opening through which the guide wire 603 extends. A spring 694 is positioned next to the support plate 696. The spring 694 pushes against the support plate 696 and the support plate 696 supports the spring 694 to allow the spring 694 to compress and expand.

Figure 22:
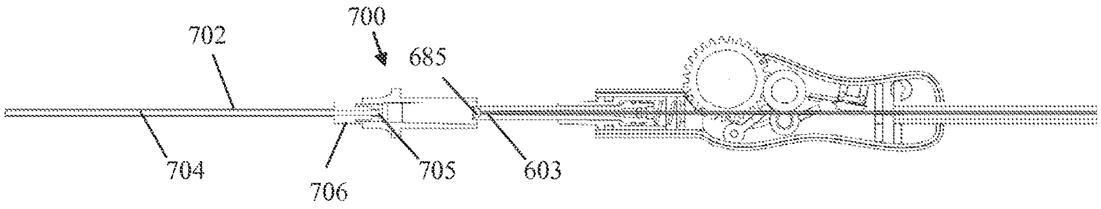
FIG. 22 is a side view of the introducer of FIG. 19.
Figure 23:
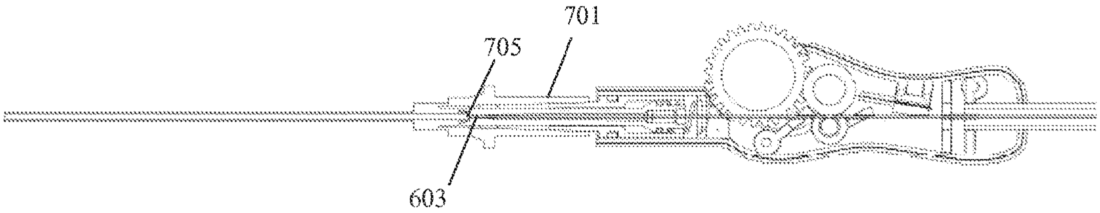
FIG. 23 is a side view of the introducer of FIG. 19.

A needle mating apparatus is provided at the front end housing 604. The needle mating apparatus includes a needle mating tip 680, a slip connector 682, and a spring 694. The needle mating apparatus is configured to receive and mate with a standard needle assembly 700, such as shown in FIGS. 22-23. The needle assembly 700 includes a needle 704, a cannulated housing or flash chamber 701 and a hub 706. The flash chamber 701 is tubular and has a front end portion that mates with the hub 706 and rear end portion that mates with the slip connector 682. The needle mating tip 680 extends inside the flash chamber 701 and mates with the needle 704.

The slip connector 682 is a single piece device that has a front end portion, mid-portion and rear end portion. The front end portion of the connector 682 extends out of the front end housing 604, is elongated and tapered inward from the proximal end to the distal end. The front portion and the mid-portion of the slip connector 682 share the same internal bore. The mid-portion is received inside the front end housing 604. A channel is provided about the outer circumference of the slip connector 682 at the mid-portion of the slip connector 682. The channel receives a mating lock protrusion 683 in the housing front end 604 to keep the slip connector 682 in place within the front end housing 604. The mating lock protrusion 683 extends inwardly from the interior side wall of the front end housing 604. Thus, the slip connector 682 is locked to the front end housing 604 so that it does not move. The mid-portion and the rear end portion of the slip connector 682 share the same outer diameter, which is larger than the outer diameter of the front portion of the slip connector 682. The rear end portion of the slip connector 682 has an interior central bore that has a wider diameter than the internal bore of the mid-portion and front end portion of the slip connector 682, forming a lip 691 therebetween.

The needle mating tip 680 is an elongated one-piece member having a front end portion and a rear end portion. The front end portion is elongated and has a uniform outer diameter and a central bore extending therethrough. The rear end portion has a larger outer diameter than the front end portion and has an angled surface 681 that is angled downward from the rear end portion to the front end portion.

The rear end portion 684 of the needle tip 680 has a channel that receives a gasket 690. The gasket 690 is made of rubber to prevent fluid from passing. The guide wire 603 passes through the gasket 690 and prevents blood or fluid from flowing back into the housing 602 during operation. Another rubber gasket can be fitted about the guide wire 603 and stay inside the rear end of the needle mating tip 680 to further prevent blood or fluid from flowing back into the housing 602 during operation. The proximal or rear end portion 684 of the needle tip 680 has a reduced end portion that forms an internal lip 688. The spring 694 extends around the reduced end portion inside the slip connector 682 and pushes against the lip 688. Thus, the spring 694 biases the needle tip 680 outward and compresses inward when the needle tip 680 is pushed by the user, to ensure that the needle connector 680 remains properly mated with the needle.

A central bore extends through the needle mating tip 680 to receive the guide wire 603. The rear end portion of the needle mating tip 680 has an enlarged internal central bore with a gasket 692. The gasket 692 is made of rubber and also prevents blood or fluid from flowing back into the housing 602. The enlarged bore section can be tapered to guide the guide wire 603 through the needle mating tip 680.

As shown in FIGS. 19-22, the mating tip 680 is at least partially positioned inside the slip connector 682. More specifically, the elongated front end portion of the needle mating tip 680 extends through the central bore of the front end portion and mid-portion of the slip connector 682. The rear end portion of the needle mating tip 680 remains in the rear end portion of the slip connector 682. The spring 694 pushes against the lip 688 of the reduced outer rear end portion of the slip connector 682 to bias the needle mating tip 680 forward in the slip connector 682. The spring 694 can push the needle mating tip 680 to the forward-most position, where the angled surface 681 of the needle mating tip 680 contacts the lip 691 of the slip connector 682, as shown.

Thus, the slip connector 682 receives the needle mating tip 680 and prevents the needle mating tip 680 from falling out of the front end housing 604. In addition, the slip connector 682 allows the needle mating tip 680 to move inward and outward under force of the spring 694.

Referring to FIGS. 22, 23, the flash chamber 701 is frictionally fit to the slip connector 682. More specifically, the rear end of the flash chamber 701 slides over the top of the front end portion of the needle mating tip 680 and is frictionally received by the outer surface of the tapered front end portion of the slip connector 682. When the needle assembly 700 is fit to the slip connector 682, the internal bore of the needle mating tip 680 is aligned with the distal end 705 of the needle 704, which protrudes backward from the inside of the hub 706. The distal end 705 enters a small hole 685 in the nose of the needle mating tip 680. The hole 685 is tapered inward to guide the needle end 705 toward the bottom of the hole 685. Accordingly, the guide wire 603 is aligned with the proximal rear end 705 of the needle 704. Thus, when the user moves the guide wheel assembly 610 forward in direction Y, the guide wire 603 moves forward in the needle mating tip 680 into the central bore of the needle 704.

It is important that the distal end of the needle mating tip 680 be aligned with and abut or nearly abut the extreme proximal end of needle 704, so that that guide wire 603 can enter the needle 704 without stubbing the needle 704. However, different manufacturers offer flash chambers 701 having different lengths. The needle mating apparatus is able to mate with flash chambers 701 of different lengths. When the flash chamber 701 is pressed onto the slip connector 682, the flash chamber 701 will push the needle mating tip 680 backward or inward into the front housing 604 against the force of the spring 694. The amount that the needle mating tip 680 is pushed is dependent on the length of the flash chamber 701. Longer flash chamber 701 will not push the mating tip 680 very far, and shorter flash chambers 701 will push the mating tip 680 further. The spring 694 ensures that the needle end 705 remains reliably seated in the hole 685 and abutted against the bottom of the hole 685 of the needle mating tip 680 and that the needle end 705 is aligned with the central bore of the needle mating tip 680.

As shown, a sheath 601 is positioned outside the housing 602 and extends into an opening at the rear end housing 606. The sheath 601 protects the guide wire 603. The guide wire 603 extends through the sheath 601, the housing 602 and the male end connector 680. More specifically, the guide wire 603 extends through the entire housing 602. It enters together with the sheath 601 through an opening in the rear end housing 606. The sheath 601 terminates once inside the housing 602, and the wire 603 continues from the rear end housing 606 to the front end housing 604, where it is supported by the guides 630, 640, 650, 660 and passes through the tap 615 in the guide wheels 611*a*, 611*b*. At the front end housing 604, the wire 603 passes through the support plate 696 opening, through the spring, and into the enlarged bore at the rear end portion of the needle mating tip 680. The guide wire 603 then passes through the central bore of the needle mating tip 680 and out of the front of the tip 680. As the wire 603 passes through the rear end housing 606, it extends through the retainer assemblies 630, 640, 650, 660, and between the drive wheel 616 and the peg 652.

In operation, the slip connector 682 and needle mating tip 680 are inserted into the tubular front end housing 604 and locked in place. The needle mating tip 680 is advanced to the point at which the needle mating tip 680 comes into contact with the back end of the needle. This mating tip then slides through the slip connector 682. The spring 694 keeps the tip flush against the needle to guide the wire 603 during normal operation. As shown in FIG. 22, the needle assembly 700 can then be placed over the needle mating tip 680 and/or connector interlock 682. The needle assembly 700 is aligned with the needle mating tip 680 so that the orifices are aligned. The needle assembly 700 fits snugly over the connector interlock 682 and the needle mating tip 680 fits snug against the back of the needle. This aligns the needle 704 with the nose of the needle mating tip 680, so that the rear end 705 of the needle 704 is seated in the hole 685 at the nose of the needle mating tip 680. The guide wire 603 can then be extended through the housing 602 and into the rear end of the needle mating tip 680. After the needle assembly 700 is in place, the wire 603 can then be extended through the needle 702 by operation of the wheel assembly 610.

The user then places the needle 704 into the patient, such as the vein or artery lumen, similar to the manner discussed with respect to FIGS. 1-18 above. Once the needle 704 is placed, the user rotates the guide wheel assembly 610 in the insertion direction Y (FIG. 20). This can be done using a single hand of the user. Since the needle is already positioned in the vein, the user rotates the wheel 610, which is easy to reach because it is at the front end of the housing 602. Thus, the user can hold the rear end housing 604 in the palm of the hand and (without moving his hand) operate the wheel assembly 6120 with a single finger (such as the index finger). In addition, the user holds the device 600 steady (i.e., it does not have to be moved forward, but rather the housing 602 remains stationary while the user rotates the wheel assembly 610) and allows the movement of the wheel 610 to advance the guide wire 603, so that single-handed operation is possible. Single-handed operation is further made possible by the contour shape of the hub. Thus, the user can hold an ultrasound probe in the other hand to assist placement of the guide wire 603 and catheter.

That action by the user causes the wheel 614 to rotate in direction Y with respect to the housing 602, which in turn moves the drive wheel 616 by operation of the guide wheel teeth 612 and the drive wheel teeth 618. The gasket 619 (FIG. 21) on the outer surface of the drive wheel 616 forces the guide wire 603 forward, through the housing 602 and into the patient. Notably, the present embodiment of FIGS. 19-23 does not require a drive wire, as in the embodiment of FIGS. 1-10 above.

Once the guide wire 603 has entered the user's vein (about 1-2.5 inches depending on catheter length), the user pushes the hub 706 forward to force the catheter 702 off the needle 704 and into the patient (see FIG. 8, for instance). The catheter can be pushed into the patient further than the needle and/or guide wire 603 since it is more flexible and won't puncture the side of the vein or vessel. The user can then remove the needle 704 and guide wire 603 from the patient, leaving the catheter 702 and hub 706 properly placed in the patient. The user can then connect a syringe, IV device or other medical instrument at the rear end of the hub 706.

It is noted that the apparatus 600 is described as having a guide wheel assembly 610 and a separate drive wheel 616. However, the invention need not have a separate drive wheel 616, and instead the guide wheel 610 can contact the guide wire 603 and move the guide wire 603 forward. For instance, the outer circumference of the guide wheel 611 can be coated with rubber or the like that directly contacts the guide wire 603 to move the guide wire 603 forward. Or, the outer circumference of the spacing plate 613 can be coated with rubber or have a rubber materials, and that surface can directly contact the guide wire 603 to move the guide wire forward.

Figure 12:
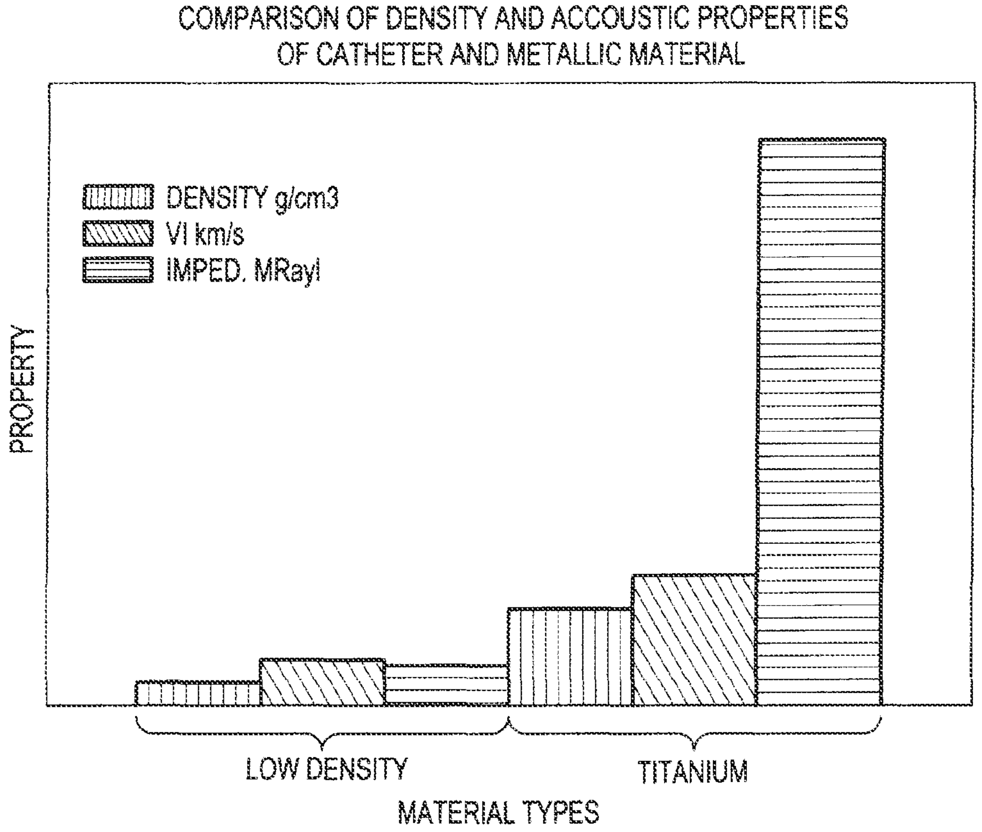
FIG. 12 is a graph showing UV detectable materials.

The Visible Catheter 300 (FIGS. 11-12)

Another object of the invention is to provide a catheter, both central and peripheral, that can be visualized by ultrasound, to enable correct placement to be determined and recorded by ultrasound visualization. Catheters, both central and peripheral, which are easily visualized by ultrasound, enable correct placement to be determined and recorded by ultrasound visualization.

It is noted that current catheter materials cannot be detected by ultrasound. In the present embodiment of the invention, the catheter 300 is constructed of materials that can be easily visualized under ultrasound. For instance metals, ceramics, or compounds (like barium sulfate or titanium), can be integrated within the structure of the catheter material allowing for direct visualization of catheter placement with the ultrasound. As an example, one could confirm by ultrasound that a catheter intended to be placed in a vein is in fact located in a vein and not in an artery or outside any blood vessel.

Ultrasound properties are material dependent. The sound velocities and impedance values of typical catheter materials such as plastics, urethanes or rubbers are very low (0.959-2.06 km/s and 1.41-2.00 MRayl) compared to metals such as, aluminum, copper and Titanium (5.01-6.3 km/s and 17.0-44.6 Mrayl). The properties for low density polyethylene and Titanium are compared in FIG. 12. This demonstrates that as the density of a material changes, so do it's acoustic properties. Materials of different densities will appear as distinct and different in an ultrasound image.

In yet another embodiment of the invention, the outer surface 304 of the catheter is coated with metallic material such as Titanium, the catheter. This makes the catheter 300 detectable by ultrasound, because the high impedance surface will reflect some of the sound. A specific length of the catheter to be detected by ultrasound is coated with a metallic coating, such as by using sputtering. Thus, only a portion (the front end) of the catheter 300 can be coated or made of UV visible materials. Sputtering is a Physical Vapor Deposition vacuum process used to deposit very thin films onto a substrate for a wide variety of commercial and scientific purposes. Sputtering occurs when an ionized gas molecule is used to displace atoms of a specific material. These atoms then bond at the atomic level to a substrate and create a thin film. Several types of sputtering can be used, including: ion beam, diode, and magnetron sputtering. Sputtering units are available commercially and not only they can help in coating a variety of metallic materials, but the thickness of the coating can also be measured during the sputtering process. The coating thickness is typically in Angstroms. Preferably, Titanium is used best mode, because of its biocompatibility and excellent corrosion resistance to a broad range of possible corroding media that may be encountered in the field of medicine.

It is noted that the catheter 300 and the introducer 10 (FIGS. 1-10) of the invention have separate utility and need not be utilized together. For instance, the catheter 300 can be utilized with any catheter introduction set, and not only the introducer 10 of the present invention. In addition, the introducer 10 can be used to place any conventional catheter, and need not be utilized with the catheter 300 of the present invention. Not withstanding those separate uses, the catheter 300 and introducer 10 of the invention have certain advantages when utilized together (FIGS. 1-10). Because the catheter 300 is visible to UV detection and the introducer 10 allows the user to perform IV insertion with a single hand, the user can perform UV detection at the same time he/she is inserting an IV into the patient. Thus, the user can confirm proper placement of the needle 202, as well as the catheter 300, during and immediately after insertion. The user can perform the catheter 300 placement with a single hand using the introducer 10, and with the other hand can track placement of the needle 202 and the catheter 300 in the patient.

Probe Cover 400

Figure 13:
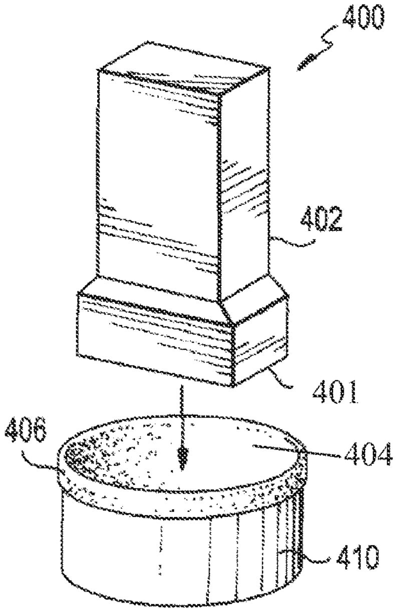
FIG. 13 is a perspective view of a probe cover assembly prior to being applied to a probe in accordance with another embodiment of the invention.
Figure 14:
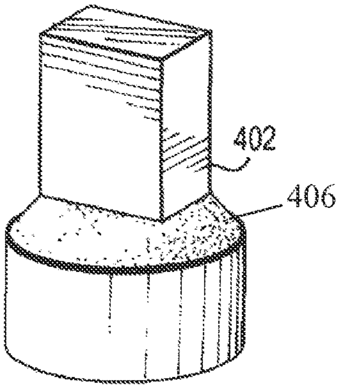
FIG. 14 shows the cover assembly of FIG. 13 fitted to a probe.
Figure 15:
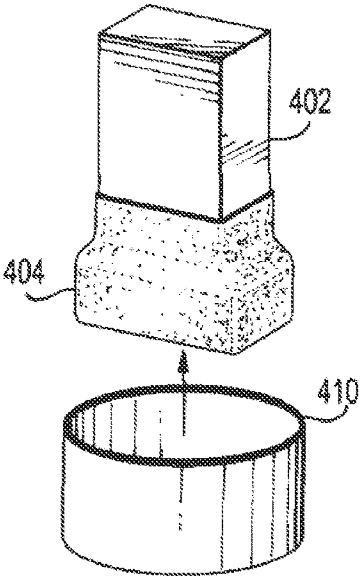
FIG. 15 shows the container removed from the cover with the probe ready to be used.

Another embodiment of the invention is shown in FIGS. 13-15. A sterile cover set 400 is provided that can be placed over the transducer end of a piece of medical equipment, such as an ultrasound probe 402. The sterile probe cover set 400 includes a sterile probe cover 404 and a container 410. The cover 404 is open at the top (i.e., no lid or cover) and can be made of rubber or latex for instance, can have the general shape of the probe 402 and is sized to fit snugly over the probe 402. In the embodiment shown, the cover 404 is shaped like a bag, with a bottom and sides and can optionally match the shape of the probe end 401. The container 410 can have a similar shape as the cover 404 and is slightly wider than the cover 404. The container 410 is shorter than the cover 404 so that the tops 406 of the sides extend beyond the top of the sides of the container 410. In the current embodiment, the container 410 can be a circular piece, with a bottom and sides, or can be a tube with no bottom, or can have a rectangular shape. The container 410 can optionally match the shape of the probe end 401. The container 410 can be made of cardboard or from hard plastic or other material which can maintain its shape and the shape of the rubber sterile probe cover 404. The container 410 is wider than the probe and the cover 404, so that the cover 404 is stretched and can be easily fit over the end 401 of the probe 402.

The cover 404 is pre-assembled to be inside the container 410, and the top sides 406 of the cover 404 are stretched and folded down over the top sides of the container 410. The container 410 and cover 404 are packaged in a sealed plastic bag, and the entire packaging is sterilized.

When the probe 402 is ready to be used, the user opens the sealed plastic bag and removes the container 410 with the cover 404 positioned inside of the container 410. The user should preferably hold the assembly by the container 410. However, only the inside of the cover 404 is exposed (since the cover is turned inside-out at the top sides 406), so the user can touch the cover 404 without contaminating the outside of the cover 404.

As shown in FIG. 13, the user then pushes the container 410 and cover 404 over the end of the probe 402, so that the sterile probe cover 404 is wrapped around the probe 402. Optionally, ultrasound gel can be placed on the surface of the sterile probe cover prior to placing it on the ultrasound probe. Referring to FIG. 14, the cover 404 and container 410 are positioned over the probe 402. The top sides 406 of the cover 404 are then folded up, off of the container 410 and onto the probe 410. Because the top sides 406 were stretched to fit over the container 410, the top sides 406 will retract inward and form a snug fit on the probe end 401. At this point, the cover 404 is on the probe 402. Referring to FIG. 15, the container 410 is then removed from the probe 402, leaving the sterile probe cover 404 on the probe transducer end 402. During the process, the sterile probe cover remains sterile, because the operator only touches the container 410. The sterile probe cover 404 is never touched by the operator.

It should be appreciated that the assembly 400 can be preassembled so that the top portion 406 is folded downward over the top of the container 410. The cover 404 may need to be stretched in order to do so, and so that the cover 404 fits the probe. In accordance with one embodiment of the invention, the probe cover is less than 3 inches deep, 4 inches in width and 4 inches in height. It will be appreciated that while a snug fitting cover 404 is provided in the current embodiment, a longer and looser fitting cover 404 can be provided that is secured to the probe 402 by rubber bands or the like.

The Ultrasound Introducer Kit

One object of the invention is to provide a catheter introduction set that is particularly well suited for use with a single hand. The catheter introduction set includes a proximal end and a distal end, with the proximal end able to couple with a needle. The introducer device can either come packaged and mated with a catheter and introducer needle, or be mated by the user with another prepackaged needle. To enable single-handed use, the means to control the guidewire is located within the proximal two-thirds of the catheter introduction set. An additional inventive step enabling single-handed use is the introduction of cannula progression means that are located within the proximal two-thirds of the catheter introduction set.

Figure 16:
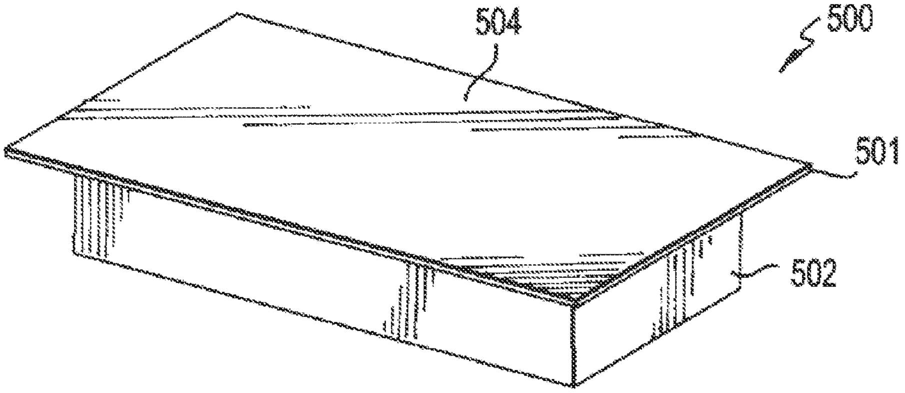
FIG. 16 shows a UV assisted introducer kit in accordance with another embodiment of the invention.
Figure 17:
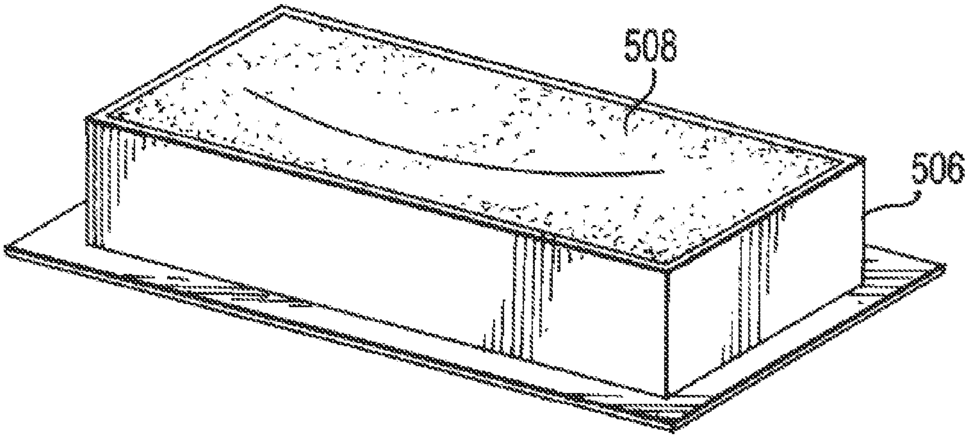
FIG. 17 is a bottom view of the kit of FIG. 16.
Figure 18:
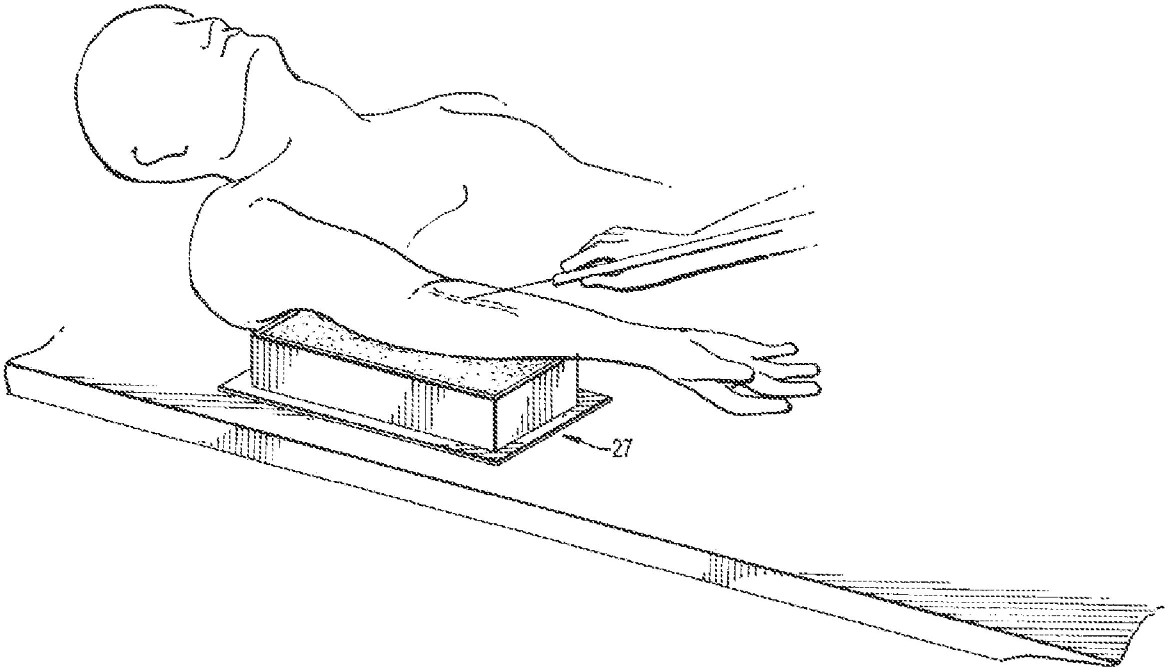
FIG. 18 shows the patient resting an arm on the kit of FIG. 16.

Turning to FIGS. 16-18, another embodiment of the invention is shown. Here, an introducer kit 500 is provided. The kit 500 includes a case or box 501 having a base 502 and a lid or top 504. The box 501 is rectangular in shape and the top 504 is larger than the base 502 so that it is easy to remove the top 504. As best shown in FIG. 17, the box also has a bottom 506. A pad 508 is provided at the exterior surface of the bottom 506. The pad 508 can be at a portion of the bottom 506 or extend the entire width and height of the bottom 506. Referring to FIG. 18, the patient can rest his/her arm on the pad 508 during IV placement or other medical procedure. The pad 508 stabilizes a body part that is to be catheterized. In the embodiment shown, the pad 508 of the kit case 500 stabilizes the patient's arm at the elbow to assist in catheterization of the anti-cubital veins. In an alternative embodiment of the invention, the bottom 506 can have a concave shape instead of a pad 508.

The box 501 has an interior space that is used to retain medical equipment that is useful for a medical practitioner to perform a medical process, in particular an ultrasound assisted vessel cannulation. Thus, the kit 500 includes all the single-use components necessary for ultrasound assisted vessel cannulation, including: catheter introducer 10 (FIGS. 1-10); catheter tubing 300 (FIG. 11); probe cover set 400 (FIGS. 13-15); lidocaine solution; sterilizing solution and applicator; suture material; suturing needle; gauze pads; scalpel; drape with adhesive; towel; sterile US gel packet; two rubber bands; directional marker; normal saline flush; and tourniquet. It will be appreciated, however, that the kit 500 need not include every single element listed here, and still be within the spirit and scope of the invention. In particular, the introducer 10, catheter tubing 300, and probe cover set 400 of the invention need not be provided with the kit 500, and any conventional introducer, catheter tubing and probe cover can be provided. The box 501 and its contents can be placed in a heat-sealed plastic bag and sterilized.

For use in vessel cannulation, the patient is first placed in a recumbent position. After the contents are removed from the sterile package the box 501 is flipped so that the ergonomically designed bottom faces up and the elbow is placed on this surface to facilitate stabilization for cannulation. The kit keeps all necessary materials located in a single convenience place in a sterile manner. The box 501 provides arm stabilization for safe and successful cannulation.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A wire introduction device comprising:

a housing comprising:

a rear housing end;

a front housing end connected at a front end of the rear housing end;

a front opening in the front housing;

a drive wheel assembly positioned in the rear housing end;

a support plate positioned in the front housing end proximate the front end of the rear housing end;

a slip connector having a slip connector rear portion and a slip connector mid-portion that are positioned within the front housing end proximal of the front opening of the housing and a slip connector front portion that extends distally from the front opening of the housing;

a needle mating tip configured to receive a needle assembly and extend through the slip connector and through the front opening of the housing; and a spring received in the front housing and configured to bias the needle mating tip and the front portion of the slip connector to extend through the front opening of the housing.

2. The wire introduction device of claim 1, wherein the support plate is substantially annular with a central opening configured to allow a guide wire to extend there through.

3. The wire introduction device of claim 1, wherein:

the spring is positioned adjacent to the support plate to press against the support plate.

4. The wire introduction device of claim 3, wherein the slip connector is positioned forward of the spring, such that the spring is configured to be compressed between the support plate and the slip connector.

5. The wire introduction device of claim 1, wherein the rear housing end is ergonomically shaped to be grasped by a user's hand, wherein the front housing end is annular, and wherein the support plate is annular.

6. The wire introduction device of claim 1, comprising a guide wheel assembly positioned in the rear housing end.

7. The wire introduction device of claim 6, wherein the guide wheel assembly includes opposite guide wheels rotatably supported in the rear housing and partially exposed through a middle opening of the rear housing.

8. The wire introduction device of claim 7, wherein the guide wheel assembly includes a spacer plate disposed between the opposite guide wheels and defining a radial space between the opposite guide wheels.

9. The wire introduction device of claim 8, wherein the radial space is configured to permit a guide wire to pass through between the opposite guide wheels.

10. The wire introduction device of claim 7, wherein the drive wheel assembly includes a drive wheel rotatably mounted in the rear housing and engaged with one of the opposite guide wheels.

11. The wire introduction device of claim 10, wherein rotation of the opposite guide wheels is configured to cause the drive wheel to rotate.

12. The wire introduction device of claim 10, wherein the drive wheel assembly includes a wheel plate connected to the drive wheel, the wheel plate includes a circumferential surface that is configured to contact a guide wire.

13. The wire introduction device of claim 12, wherein the wheel plate has an outer circumference that includes a frictional material configured to grip the guide wire.

14. The wire introduction device of claim 12, and further comprising a contact peg in the rear housing and configured to engage a guide wire against the wheel plate.

15. The wire introduction device of claim 14, wherein the wheel plate contacts a top side of the guide wire and the peg contacts a bottom side of the guide wire.

16. The wire introduction device of claim 12, wherein, a guide wire moves longitudinally responsive to rotation of the opposite guide wheels.

17. The wire introduction device of claim 12, wherein a portion of the drive wheel is located outside of a top opening in the rear housing.

18. The wire introduction device of claim 1, and further comprising a plurality of guide assemblies positioned in the rear housing end and along a length of a guide wire.

19. The wire introduction device of claim 1, and further comprising a rear opening located at a rear end of the rear housing, wherein a guide wire extends through the rear opening.

20. The wire introduction device of claim 19, and further comprising a sheath positioned around the guide wire at the rear opening of the rear housing.

21. The wire introduction device of claim 1, wherein the slip connector mid-portion and the slip connector rear portion each have a first outer diameter that is larger than a second outer diameter of the slip connector front portion.

22. The wire introduction device of claim 1, wherein the slip connector rear portion has an interior central bore that a rear portion bore diameter that is wider than a distal bore diameter that extends through the slip connector mid-portion and slip connector front portion.

* * * * *